US007723338B2

(12) United States Patent
Chen et al.

(10) Patent No.: US 7,723,338 B2
(45) Date of Patent: *May 25, 2010

(54) CRYSTALLINE FORMS OF 1-BENZOYL-4-[2-[4,7- DIMETHOXY-1-[(PHOSPHONOOXY) METHYL]-1H-PYRROLO[2,3-C]PYRIDIN-3-YL]-1,2-DIOXOETHYL]-PIPERAZINE

(75) Inventors: Chung-Pin H. Chen, Madison, CT (US); Qi Gao, Wallingford, CT (US); David K. Leahy, Morristown, NJ (US); Srividya Ramakrishnan, Milltown, NJ (US); Venkatramana M. Rao, Edison, NJ (US); Anne I. Song, Fairfield, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 308 days.

This patent is subject to a terminal disclaimer.

(21) Appl. No.: 11/340,032

(22) Filed: Jan. 26, 2006

(65) Prior Publication Data

US 2006/0172974 A1     Aug. 3, 2006

Related U.S. Application Data

(60) Provisional application No. 60/648,579, filed on Jan. 31, 2005.

(51) Int. Cl.
*A61K 31/497* (2006.01)
*C07D 241/04* (2006.01)
*C07D 295/00* (2006.01)

(52) U.S. Cl. .................. 514/252.12; 544/358
(58) Field of Classification Search .................. None
See application file for complete search history.

(56) References Cited

U.S. PATENT DOCUMENTS

| 6,476,034 B2 | 11/2002 | Wang et al. |
| 6,632,819 B1 | 10/2003 | Wang et al. |
| 2005/0209246 A1 | 9/2005 | Ueda et al. |

OTHER PUBLICATIONS

Vippagunta et al. Advanced Drug Delivery Reviews, 2001, 48, 3-26.*
Borisy et al. PNAS, 2003, 100(13), 7977-82.*

* cited by examiner

*Primary Examiner*—James O Wilson
*Assistant Examiner*—Noble Jarrell
(74) *Attorney, Agent, or Firm*—John F. Levis

(57) ABSTRACT

The instant disclosure provides crystalline forms of 1-benzoyl-4-[2-[4,7-dimethoxy-1-[(phosphonooxy)methyl]-1H-pyrrolo[2,3-c]pyridin-3-yl]-1,2-dioxoethyl]-piperazine, salts and solvates thereof. The present disclosure also generally relates to pharmaceutical compositions comprising the crystalline form(s), as well of methods of using the crystalline form(s) in the treatment of HIV and/or AIDS, and methods for obtaining such crystalline form(s).

12 Claims, 32 Drawing Sheets

PXRD: Form N-2 Free Acid

DSC: Form N-2 Free Acid

TGA: Form N-2 Free Acid

Atomic Labels: Form N-2 Free Acid

Moisture-Sorption Isotherms: Form N-2 Free Acid

PXRD: Form H-1 Free Acid

DSC: Form H-1 Free Acid

TGA: Form H-1 Free Acid

Atomic Labels: Form H-1 Free Acid

Moisture-Sorption Isotherm: Form H-1 Free Acid

PXRD: Form Hemi-Calcium Salt H4-1

DSC: Form Hemi-Calcium Salt H4-1

TGA: Form Hemi-Calcium Salt H4-1

Atomic Labels: Form Hemi-Calcium Salt H4-1

Moisture-Sorption Isotherm: Form Hemi-Calcium Salt H4-1

PXRD: Form Hemi-Magnesium Salt H4-1

DSC: Form Hemi-Magnesium Salt H4-1

TGA: Form Hemi-Magnesium Salt H4-1

Atomic Labels: Form Hemi-Magnesium Salt H4-1

Moisture-Sorption Isotherm: Form Hemi-Magnesium Salt H4-1

PXRD: Form Mono-Magnesium Salt P-3

DSC: Form Mono-Magnesium Salt P-3

TGA: Form Mono-Magnesium Salt P-3

PXRD: Form Hemi-Magnesium Salt P-2

DSC: Form Hemi-Magnesium Salt P-2

TGA: Form Hemi-Magnesium Salt P-2

PXRD: Form Mono-Lysine Salt P-2

DSC: Form Mono-Lysine Salt P-2

TGA: Form Mono-Lysine Salt P-2

PXRD: Form Mono-Lysine Salt P-1

DSC: Form Mono-Lysine Salt P-1

TGA: Form Mono-Lysine Salt P-1

CRYSTALLINE FORMS OF 1-BENZOYL-4-[2-[4,7-DIMETHOXY-1-[(PHOSPHONOOXY) METHYL]-1H-PYRROLO[2,3-C]PYRIDIN-3-YL]-1,2-DIOXOETHYL]-PIPERAZINE

CROSS-REFERENCE TO RELATED APPLICATIONS

This application claims the benefit of U.S. Provisional Application Ser. No. 60/648,579 filed Jan. 31, 2005.

FIELD OF THE INVENTION

The present disclosure relates to crystalline forms of 1-benzoyl-4-[2-[4,7-dimethoxy-1-[(phosphonooxy)methyl]-1H-pyrrolo[2,3-c]pyridin-3-yl]-1,2-dioxoethyl]-piperazine, salts and solvates thereof. The present disclosure also generally relates to pharmaceutical compositions comprising the crystalline form(s), methods of using the crystalline form(s) in the treatment of HIV and/or AIDS, and methods for obtaining such crystalline form(s).

BACKGROUND OF THE INVENTION

HIV-1 (human immunodeficiency virus-1) infection remains a major medical problem, with an estimated 42 million people infected worldwide at the end of 2002. The number of cases of HIV and AIDS (acquired immunodeficiency syndrome) has risen rapidly. In 2002, ~5.0 million new infections were reported, and 3.1 million people died from AIDS. Currently available drugs for the treatment of HIV include nine nucleoside reverse transcriptase (RT) inhibitors or approved single pill combinations (zidovudine or AZT (or Retrovir®), didanosine (or Videx®), stavudine (or Zerit®), lamivudine (or 3TC or Epivir®), zalcitabine (or DDC or Hivid®), abacavir succinate (or Ziagen®), Tenofovir disoproxil fumarate salt (or Viread®), Combivir® (contains –3TC plus AZT), Trizivir® (contains abacavir, lamivudine, and zidovudine); three non-nucleoside reverse transcriptase inhibitors: nevirapine (or Viramune®), delavirdine (or Rescriptor®) and efavirenz (or Sustiva®), and eight peptidomimetic protease inhibitors or approved formulations: saquinavir, indinavir, ritonavir, nelfinavir, amprenavir, lopinavir, Kaletra® (lopinavir and Ritonavir), and Atazanavir (Reyataz®). Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present (Larder and Kemp; Gulick; Kuritzkes; Morris-Jones et al; Schinazi et al; Vacca and Condra; Flexner; Berkhout and Ren et al; (Ref. 6-14)). Therefore, novel anti-HIV agents exhibiting distinct resistance patterns, and favorable pharmacokinetic as well as safety profiles are needed to provide more treatment options.

U.S. Pat. No. 6,476,034 (incorporated herein by reference in its entirety) and U.S. Pat. No. 6,632,819 (incorporated herein by reference in its entirety) disclose a class of compounds (or pharmaceutically acceptable salts thereof) of the formula

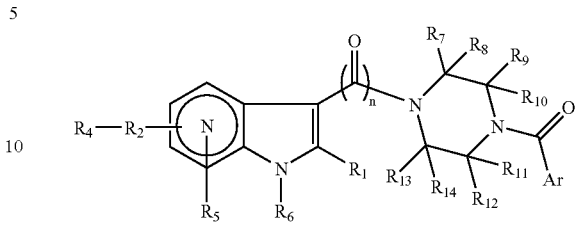

wherein:

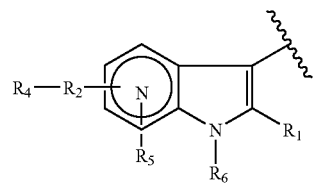

is selected from the group consisting of

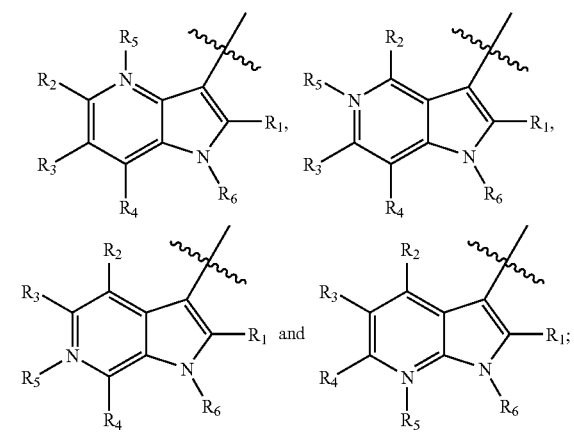

$R_1$, $R_2$, $R_3$, $R_4$ are each independently selected from the group consisting of H, $C_1$-$C_6$ alkyl, $C_3$-$C_6$ cycloalkyl, $C_2$-$C_6$ alkenyl, $C_4$-$C_6$ cycloalkenyl, $C_2$-$C_6$ alkynyl, halogen, CN, phenyl, nitro, $OC(O)R_{15}$, $C(O)R_{15}$, $C(O)OR_{16}$, $C(O)NR_{17}R_{18}$, $OR_{19}$, $SR_{20}$ and $NR_{21}R_{22}$;

$R_{15}$ is independently selected from the group consisting of H, $C_1$-$C_6$ alkyl, $C_3$-$C_6$ cycloalkyl, $C_2$-$C_6$ alkenyl and $C_4$-$C_6$ cycloalkenyl;

$R_{16}$, $R_{19}$, and $R_{20}$ are each independently selected from the group consisting of H, $C_1$-$C_6$ alkyl, $C_{1-6}$ alkyl substituted with one to three halogen atoms, $C_3$-$C_6$ cycloalkyl, $C_2$-$C_6$ alkenyl, $C_4$-$C_6$ cycloalkenyl, and $C_3$-$C_6$ alkynyl; provided the carbon atoms which comprise the carbon-carbon triple bond of said $C_3$-$C_6$ alkynyl are not the point of attachment to the oxygen or sulfur to which $R_{16}$, $R_{19}$, or $R_{20}$ is attached;

$R_{17}$ and $R_{18}$ are each independently selected from the group consisting of H, $C_1$-$C_6$ alkyl, $C_3$-$C_6$ cycloalkyl, $C_3$-$C_6$ alkenyl, $C_4$-$C_6$ cycloalkenyl, and $C_3$-$C_6$ alkynyl; provided the carbon atoms which comprise the carbon-carbon double bond of said $C_3$-$C_6$ alkenyl or the carbon-carbon triple bond of said $C_3$-$C_6$ alkynyl are not the point of attachment to the nitrogen to which $R_{17}$ and $R_{18}$ is attached;

$R_{21}$ and $R_{22}$ are each independently selected from the group consisting of H, OH, $C_1$-$C_6$ alkyl, $C_3$-$C_6$ cycloalkyl, $C_3$-$C_6$ alkenyl, $C_5$-$C_6$ cycloalkenyl, $C_3$-$C_6$ alkynyl, and $C(O)R_{23}$; provided the carbon atoms which comprise the carbon-carbon double bond of said $C_3$-$C_6$ alkenyl, $C_4$-$C_6$ cycloalkenyl, or the carbon-carbon triple bond of said $C_3$-$C_6$ alkynyl are not the point of attachment to the nitrogen to which $R_{21}$ and $R_{22}$ is attached;

$R_{23}$ is selected from the group consisting of H, $C_1$-$C_6$ alkyl, $C_3$-$C_6$ cycloalkyl, $C_2$-$C_6$ alkenyl, $C_4$-$C_6$ cycloalkenyl, and $C_2$-$C_6$ alkynyl;

$R_5$ is $(O)_m$, wherein m is 0 or 1;

n is 1 or 2;

$R_6$ is selected from the group consisting of H, $C_1$-$C_6$ alkyl, $C_3$-$C_6$ cycloalkyl, $C_4$-$C_6$ cycloalkenyl, $C(O)R_{24}$, $C(O)OR_{25}$, $C(O)NR_{26}R_{27}$, $C_3$-$C_6$ alkenyl, and $C_3$-$C_6$ alkynyl; provided the carbon atoms which comprise the carbon-carbon double bond of said $C_3$-$C_6$ alkenyl or the carbon-carbon triple bond of said $C_3$-$C_6$ alkynyl are not the point of attachment to the nitrogen to which $R_6$ is attached;

$R_{24}$ is selected from the group consisting of H, $C_1$-$C_6$ alkyl, $C_3$-$C_6$ cycloalkyl, $C_3$-$C_6$ alkenyl, $C_4$-$C_6$ cycloalkenyl, and $C_3$-$C_6$ alkynyl;

$R_{25}$ is selected from the group consisting of $C_1$-$C_6$ alkyl, $C_3$-$C_6$ cycloalkyl, $C_2$-$C_6$ alkenyl, $C_4$-$C_6$ cycloalkenyl, and $C_3$-$C_6$ alkynyl; provided the carbon atoms which comprise the carbon-carbon triple bond of said $C_3$-$C_6$ alkynyl are not the point of attachment to the oxygen to which $R_{25}$ is attached;

$R_{26}$ and $R_{27}$ are each independently selected from the group consisting of H, $C_1$-$C_6$ alkyl, $C_3$-$C_6$ cycloalkyl, $C_3$-$C_6$ alkenyl, $C_5$-$C_6$ cycloalkenyl, and $C_3$-$C_6$ alkynyl; provided the carbon atoms which comprise the carbon-carbon double bond of said $C_3$-$C_6$ alkenyl, $C_5$-$C_6$ cycloalkenyl, or the carbon-carbon triple bond of said $C_3$-$C_6$ alkynyl are not the point of attachment to the nitrogen to which $R_{26}$ and $R_{27}$ are attached;

$R_7$, $R_8$, $R_9$, $R_{10}$, $R_{11}$, $R_{12}$, $R_{13}$, and $R_{14}$ are each independently selected from the group consisting of H, $C_1$-$C_6$ alkyl, $C_3$-$C_6$ cycloalkyl, $C_2$-$C_6$ alkenyl, $C_4$-$C_6$ cycloalkenyl, $C_2$-$C_6$ alkynyl, $CR_{28}R_{29}OR_{30}$, $C(O)R_{31}$, $CR_{32}(OR_{33})OR_{34}$, $CR_{35}NR_{36}R_{37}$, $C(O)OR_{38}$, $C(O)NR_{39}R_{40}$, $CR_{41}R_{42}F$, $CR_{43}F_2$ and $CF_3$;

$R_{28}$, $R_{29}$, $R_{30}$, $R_{31}$, $R_{32}$, $R_{35}$, $R_{41}$, $R_{42}$ and $R_{43}$ are each independently selected from the group consisting of H, $C_1$-$C_6$ alkyl, $C_3$-$C_6$ cycloalkyl, $C_2$-$C_6$ alkenyl, $C_4$-$C_6$ cycloalkenyl, $C_2$-$C_6$ alkynyl and $C(O)R_{44}$;

$R_{33}$, $R_{34}$ and $R_{38}$ are each independently selected from the group consisting of H, $C_1$-$C_6$ alkyl, $C_3$-$C_6$ cycloalkyl, $C_3$-$C_6$ alkenyl, $C_4$-$C_6$ cycloalkenyl, and $C_3$-$C_6$ alkynyl; provided the carbon atoms which comprise the carbon-carbon triple bond of said $C_3$-$C_6$ alkynyl are not the point of attachment to the oxygen to which $R_{34}$ and $R_{38}$ are attached;

$R_{36}$ and $R_{37}$ are each independently selected from the group consisting of H, $C_1$-$C_6$ alkyl, $C_3$-$C_6$ cycloalkyl, $C_3$-$C_6$ alkenyl, $C_4$-$C_6$ cycloalkenyl, and $C_3$-$C_6$ alkynyl; provided the carbon atoms which comprise the carbon-carbon triple bond of said $C_3$-$C_6$ alkynyl are not the point of attachment to the nitrogen to which $R_{36}$ and $R_{37}$ are attached;

$R_{39}$ and $R_{40}$ are each independently selected from the group consisting of H, $C_1$-$C_6$ alkyl, $C_3$-$C_6$ cycloalkyl, $C_2$-$C_6$ alkenyl, $C_4$-$C_6$ cycloalkenyl, and $C_3$-$C_6$ alkynyl; provided the carbon atoms which comprise the carbon-carbon triple bond of said $C_3$-$C_6$ alkynyl are not the point of attachment to the nitrogen to which $R_{39}$ and $R_{40}$ are attached;

$R_{44}$ is selected from the group consisting of H, $C_1$-$C_6$ alkyl, $C_3$-$C_6$ cycloalkyl, $C_2$-$C_6$ alkenyl, $C_4$-$C_6$ cycloalkenyl, and $C_2$-$C_6$ alkynyl;

Ar is selected from the group consisting of

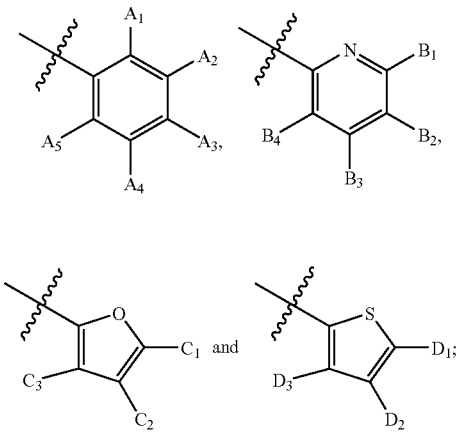

$A_1$, $A_2$, $A_3$, $A_4$, $A_5$, $B_1$, $B_2$, $B_3$, $B_4$, $C_1$, $C_2$, $C_3$, $D_1$, $D_2$, and $D_3$ are each independently selected from the group consisting of H, CN, halogen, $NO_2$, $C_1$-$C_6$ alkyl, $C_3$-$C_6$ cycloalkyl, $C_2$-$C_6$ alkenyl, $C_4$-$C_6$ cycloalkenyl, $C_2$-$C_6$ alkynyl, $OR_{45}$, $NR_{46}R_{47}$, $SR_{48}$, $N_3$ and CH(—N≡N—)—$CF_3$;

$R_{45}$ is selected from the group consisting of H, $C_1$-$C_6$ alkyl, $C_3$-$C_6$ cycloalkyl, $C_2$-$C_6$ alkenyl, $C_4$-$C_6$ cycloalkenyl and $C_3$-$C_6$ alkynyl; provided the carbon atoms which comprise the carbon-carbon triple bond of said $C_3$-$C_6$ alkynyl are not the point of attachment to the oxygen to which $R_{45}$ is attached;

$R_{46}$ and $R_{47}$ are each independently selected from the group consisting of H, $C_1$-$C_6$ alkyl, $C_3$-$C_6$ cycloalkyl, $C_3$-$C_6$ alkenyl, $C_5$-$C_6$ cycloalkenyl, $C_3$-$C_6$ alkynyl and $C(O)R_{50}$; provided the carbon atoms which comprise the carbon-carbon double bond of said $C_5$-$C_6$ alkenyl, $C_4$-$C_6$ cycloalkenyl, or the carbon-carbon triple bond of said $C_3$-$C_6$ alkynyl are not the point of attachment to the nitrogen to which $R_{46}$ and $R_{47}$ are attached;

$R_{48}$ is selected from the group consisting of H, $C_1$-$C_6$ alkyl, $C_3$-$C_6$ cycloalkyl, $C_2$-$C_6$ alkenyl, $C_4$-$C_6$ cycloalkenyl, $C_3$-$C_6$ alkynyl and $C(O)R_{49}$; provided the carbon atoms which comprise the carbon-carbon triple bond of said $C_3$-$C_6$ alkynyl are not the point of attachment to the sulfur to which $R_{48}$ is attached;

$R_{49}$ is $C_1$-$C_6$ alkyl or $C_3$-$C_6$ cycloalkyl; and $R_{50}$ is selected from the group consisting of H, $C_1$-$C_6$ alkyl, and $C_3$-$C_6$ cycloalkyl.

The same patents also specifically disclosed the compound

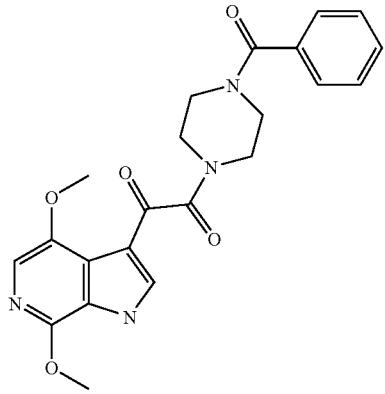

U.S. Provisional Patent Application Ser. No. 60/635,231 ("the '231 application", incorporated herein by reference in its entirety) discloses a class of compounds of the formula:

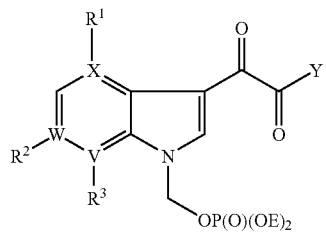

pharmaceutical compositions thereof, and their use in treating HIV infection, wherein:

X is C or N with the proviso that when X is N, V is C and $R^1$ does not exist;

W is C or N with the proviso that when W is N, $R^2$ does not exist;

V is C;

E is hydrogen or a pharmaceutically acceptable salt thereof; and

Y is selected from the group consisting of

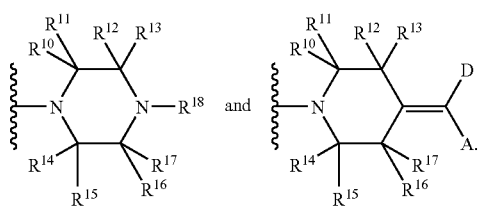

The '231 application specifically discloses

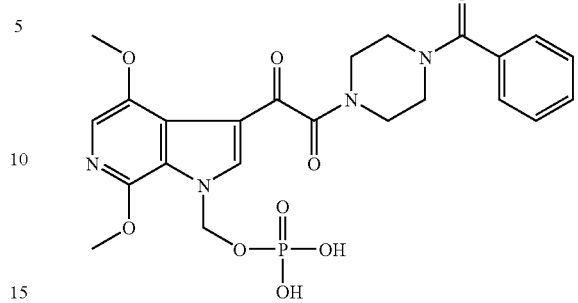

(1-benzoyl-4-[2-[4,7-dimethoxy-1-[(phosphonooxy)methyl]-1H-pyrrolo[2,3-c]pyridin-3-yl]-1,2-dioxoethyl]-piperazine) and its synthesis.

There exists a need for different forms of the compound 1-benzoyl-4-[2-[4,7-dimethoxy-1'-[(phosphonooxy)methyl]-1H-pyrrolo[2,3-c]pyridin-3-yl]-1,2-dioxoethyl]-piperazine, salts and solvates thereof, since the different forms may have different physical and/or chemical properties. There is also a need to produce a stable form of 1-benzoyl-4-[2-[4,7-dimethoxy-1-[(phosphonooxy)methyl]-1H-pyrrolo[2,3-c]pyridin-3-yl]-1,2-dioxoethyl]-piperazine, salts and solvates thereof for long term storage etc. There is also a need for reliable and reproducible methods for the manufacture, purification, and formulation to permit its feasible commercialization.

These and other aspects of the invention will become more apparent from the following detailed description.

SUMMARY OF THE INVENTION

The present disclosure provides crystalline forms of 1-benzoyl-4-[2-[4,7-dimethoxy-1-[(phosphonooxy)methyl]-1H-pyrrolo[2,3-c]pyridin-3-yl]-1,2-dioxoethyl]-piperazine, salts and solvates thereof. 1-benzoyl-4-[2-[4,7-dimethoxy-1-[(phosphonooxy)methyl]-1H-pyrrolo[2,3-c]pyridin-3-yl]-1,2-dioxoethyl]-piperazine is identified as Compound (I) herein, and is described by Formula (I):

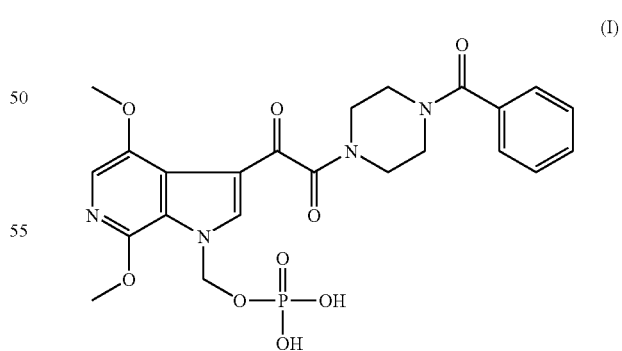

In a first embodiment, the present disclosure relates to a crystalline form of Compound (I) comprising Form N-2 Free Acid of Compound (I).

In a second embodiment, the present disclosure relates to a crystalline form of Compound (I) comprising Form H-1 Free Acid of Compound (I).

In a third embodiment, the present disclosure relates to a crystalline form of Compound (I) comprising Form Hemi-Calcium Salt H4-1 of Compound (I).

In a fourth embodiment, the present disclosure relates to a crystalline form of Compound (I) comprising Form Hemi-Magnesium Salt H4-1 of Compound (I).

In a fifth embodiment, the present disclosure relates to a crystalline form of Compound (I) comprising Form Mono-Magnesium Salt P-3 of Compound (I).

In a sixth embodiment, the present disclosure relates to a crystalline form of Compound (I) comprising Form Hemi-Magnesium Salt P-2 of Compound (I).

In a seventh embodiment, the present disclosure relates to a crystalline form of Compound (I) comprising Form Mono-Lysine Salt P-2 of Compound (I).

In an eighth embodiment, the present disclosure relates to a crystalline form of Compound (I) comprising Form Mono-Lysine Salt P-1 of Compound (I).

These and other aspects of the disclosure will become more apparent from the following detailed description.

BRIEF DESCRIPTION OF THE FIGURES

The invention is illustrated by reference to the accompanying drawings described below.

DETAILED DESCRIPTION OF THE INVENTION

Figure 1:
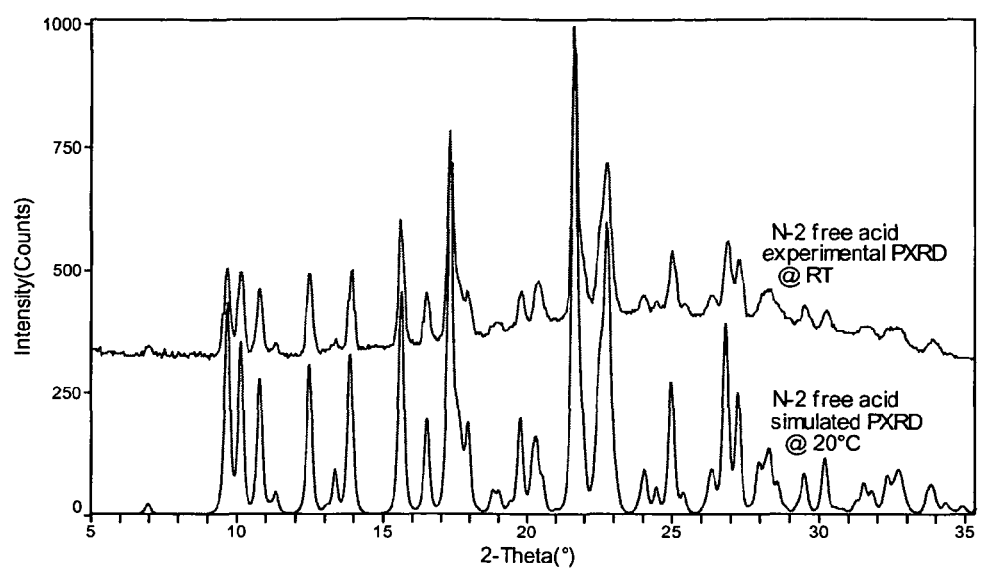
FIG. 1. illustrates experimental and simulated powdered X-ray diffraction patterns of Form N-2 of Compound (1).
Figure 2:
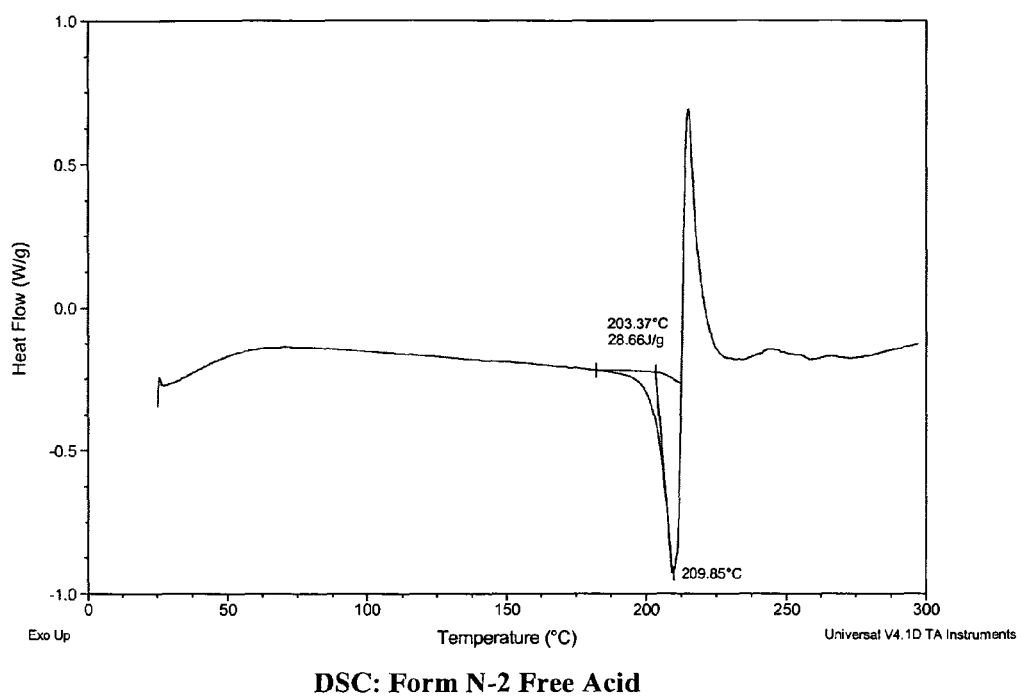
FIG. 2. illustrates differential scanning calorimetry pattern of Form N-2 of Compound (I).
Figure 3:
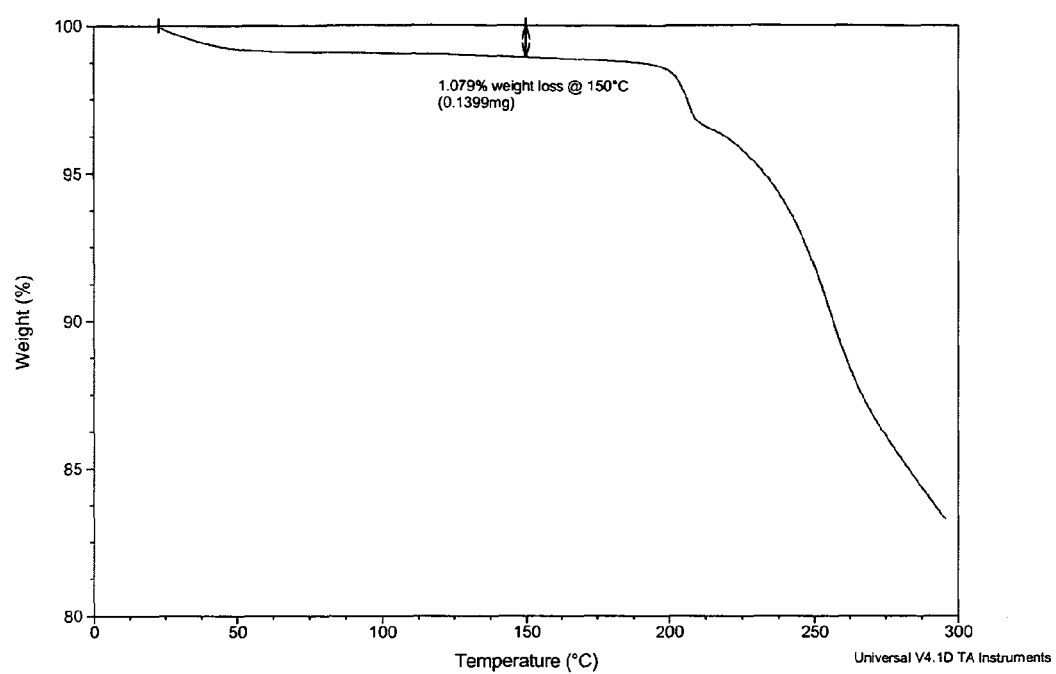
FIG. 3. illustrates thermogravimetric analysis pattern of Form N-2 of Compound (I).

The present disclosure provides, at least in part, crystalline forms of Compound (I), salts and solvates thereof. The present disclosure also generally relates to pharmaceutical compositions comprising the crystalline form(s), as well of methods of using the crystalline form(s) in the treatment of HIV and/or AIDS, and methods for obtaining such crystalline form(s). Compound (I) is 1-benzoyl-4-[2-[4,7-dimethoxy-1-[(phosphonooxy)methyl]-1H-pyrrolo[2,3-c]pyridin-3-yl]-1,2-dioxoethyl]-piperazine. Compound (I) is described by Formula (I):

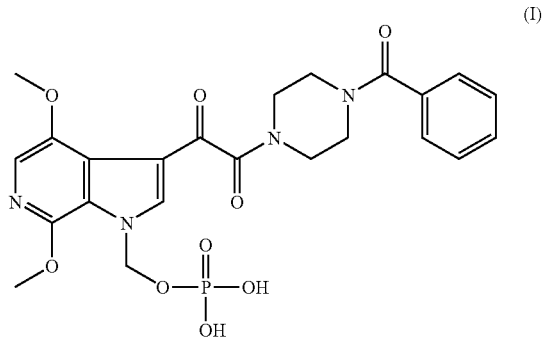

DEFINITIONS

As used herein "polymorph" refers to crystalline forms having the same chemical composition but different spatial arrangements of the molecules, atoms, and/or ions forming the crystal.

As used herein "solvate" refers to a crystalline form of a molecule, atom, and/or ions that further comprises molecules of a solvent or solvents incorporated into the crystalline lattice structure. The solvent molecules in the solvate may be present in a regular arrangement and/or a non-ordered arrangement. The solvate may comprise either a stoichiometric or nonstoichiometric amount of the solvent molecules. For example, a solvate with a nonstoichiometric amount of solvent molecules may result from partial loss of solvent from the solvate. Solvates may occur as dimers or oligomers comprising more than one molecule or Compound (I) within the crystalline lattice structure.

As used herein "amorphous" refers to a solid form of a molecule, atom, and/or ions that is not crystalline. An amorphous solid does not display a definitive X-ray diffraction pattern.

The term "pharmaceutically acceptable", as used herein, refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. In certain preferred embodiments, Compound (I) or each of its salts or solvates is in substantially pure form.

The term "substantially pure", as used herein, means a compound having a corrected purity greater than about 90% including, for example, about 91%, about 92%, about 93%, about 94%, about 95%, about 96%, about 97%, about 98%, about 99%, and about 100%.

The term "substantially in accordance", as used herein, means one skilled in the art would considered to be the same, when taken into account variables such as instrumentation limitation, and instrumentation variation, etc.

The term "substantially pure crystal", as used herein, refers to samples of crystalline forms provided with substantially pure phase homogeneity, indicating the presence of a dominant amount of a single polymorph and optionally minor amounts of one or more other polymorphs. The presence of more than one polymorph in a sample may be determined by techniques such as powder x-ray diffraction (PXRD) or solid state nuclear magnetic resonance spectroscopy. For example, the presence of extra peaks in the comparison of an experimentally measured PXRD pattern with a simulated PXRD pattern may indicate more than one polymorph in the sample. The simulated PXRDPXRD may be calculated from single crystal x-ray data. see Smith, D. K., "*A FORTRAN Program for Calculating X-Ray Powder Diffraction Patterns,*" Lawrence Radiation Laboratory, Livermore, Calif., UCRL-7196 (April 1963).

The term "slurry", as used herein, means a saturated solution of the compound, which may also contain an additional amount of the compound to afford a heterogeneous mixture of the compound and a solvent at a given temperature.

"Therapeutically effective amount" is intended to include an amount of the crystalline forms of Compound (I) that is effective when administered alone or in combination to treat HIV and AIDS. The crystalline forms of Compound (I) and pharmaceutical compositions thereof may be useful in treating HIV or AIDS. If Compound (I) is used in combination with another medication, the combination of compounds described herein may result in a synergistic combination. Synergy, as described for example by Chou and Talalay, *Adv. Enzyme Regul.* 1984, 22, 27-55, occurs when the effect of the compounds when administered in combination is greater than the additive effect of the compounds when administered alone as a single agent.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis of Compound (I):

Compound (I) may be prepared using methods well known to the skilled artisan of organic synthesis, as well as methods taught in commonly owned U.S. Provisional Patent Application No. 60/635,231 (filed Dec. 10, 2004) which is incorporated by reference herein in its entirety.

General Preparation of Crystalline Materials:

Procedures for the preparation of crystalline forms are known in the art. The crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in *Solid-State Chemistry of Drugs*, S. R. Byrn, R. R. Pfeiffer, and J. G. Stowell, $2^{nd}$ Edition, SSCI, West Lafayette, Ind. (1999).

For crystallization techniques that employ solvent, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

Suitable solvents for preparing crystals include polar and nonpolar solvents. Examples of solvents for crystallization include, for example, toluene, n-pentane, n-hexane, n-heptane, n-octane, n-decane, n-dodecane, diethyl ether, methyl tertiary-butyl ether, triethylamine, diisopropyl ether, dibutylether, 1,4-dioxane, tetrahydrofuran, chloroform, 1,1-dichloroethane, ethyl acetate, 1,2-dichloroethane, 1,2-dibromoethane, dichloromethane, butyl ethanoate, 1-butanol, 2-methyl-2-propanol, 1-propanol, 1-octanol, ethanol, methyl ethyl ketone, acetone, cyclohexanone, 2-hexanone, cyclopentanone, 2-heptanone, 4-methyl-2-pentanone, acetonitrile, butanenitrile, ethylene glycol, methanol, diethylamine, glycerol, water, methyl acetate, isopropyl acetate, butyl acetate, t-butyl acetate, hexachloroacetone, 2-butanol, t-butyl alcohol, diethylene glycol, 1-, 2-, or 3-pentanol, 2-methyl-1-propanol, and 2-butanol.

In one method to prepare crystals, a compound is suspended and/or stirred in a suitable solvent to afford a slurry, which may be heated to promote dissolution.

Seed crystals may be added to any crystallization mixture to promote crystallization. Seeding may be employed to control growth of a particular polymorph or to control the particle size distribution of the crystalline product. Accordingly, calculation of the amount of seeds needed depends on the size of the seed available and the desired size of an average product particle as described, for example, in "Programmed Cooling of Batch Crystallizers," J. W. Mullin and J. Nyvlt, *Chemical Engineering Science*, 1971, 26, 369-377. In general, seeds of small size are needed to control effectively the growth of crystals in the batch. Seed of small size may be generated by sieving, milling, or micronizing of large crystals, or by microcrystallization of solutions. Care should be taken that milling or micronizing of crystals does not result in any change in crystallinity form the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid state nuclear magnetic resonance, differential scanning calorimetry, x-ray powder diffraction, or the like, to assure formation of the preferred crystalline form of the product. The resulting crystalline form is typically produced in an amount of greater than about 70 weight % isolated yield, preferably greater than 90 weight % isolated yield, based on the weight of the compound originally employed in the crystallization procedure. The product may be comilled or passed through a mesh screen to delump the product, if necessary.

Crystalline forms may be prepared directly from the reaction medium of the final process for preparing Compound (I). This may be achieved, for example, by employing in the final process step a solvent or a mixture of solvents from which Compound (I) may be crystallized. Alternatively, crystalline forms may be obtained by distillation or solvent addition techniques. Suitable solvents for this purpose include, for example, the aforementioned nonpolar solvents and polar solvents, including protic polar solvents such as alcohols, and aprotic polar solvents such as ketones.

Characterization:

The crystalline forms of Compound (I), its salts and solvates can be characterized by a number of methods, including but not limited to, Powder X-Ray diffraction (PXRD), simulated powder X-ray patterns (Yin. S.; Scaringe, R. P.; DiMarco, J.; Galella, M. and Gougoutas, J. Z., *American Pharmaceutical Review*, 2003, 6, 2, 80), Differential scanning calorimetry (DSC) experiments, Solid-state C-13 NMR measurements, (W. L. Earl and D. L. VanderHart, *J. Magn. Reson.*, 1982, 48, 35-54), Raman spectroscopy, Infra-red spectroscopy, Moisture sorption isotherms (VTI—variable temperature isotherms), and hot stage techniques.

The forms may be characterized and distinguished using single crystal x-ray diffraction, which is based on unit cell measurements of a single crystal of a particular form at a fixed analytical temperature. A detailed description of unit cells is provided in Stout & Jensen, X-Ray Structure Determination: A Practical Guide, Macmillan Co., New York (1968), Chapter 3, which is herein incorporated by reference. Alternatively, the unique arrangement of atoms in spatial relation within the crystalline lattice may be characterized according to the observed fractional atomic coordinates. Another means of characterizing the crystalline structure is by powder x-ray diffraction analysis in which the diffraction profile is compared to a simulated profile representing pure powder material, both run at the same analytical temperature, and measurements for the subject form characterized as a series of $2\theta$ values.

One of ordinary skill in the art will appreciate that an X-ray diffraction pattern may be obtained with a measurement error that is dependent upon the measurement conditions employed. In particular, it is generally known that intensities in a X-ray diffraction pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional X-ray diffraction pattern is typically about 5% or less, and such degree of measurement error should be taken into account as pertaining to the aforementioned diffraction angles. Consequently, it is to be understood that the crystal forms of the instant invention are not limited to the crystal forms that provide X-ray diffraction patterns completely identical to the X-ray diffraction patterns depicted in the accompanying Figures disclosed herein. Any crystal forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art.

Likewise, it is to be understood that any crystal forms that provide differential scanning calorimetry (DSC), thermogravimetric annalysis (TGA), and/or moisture sorption isotherms patterns substantially identical to those disclosed in the accompanying Figures fall within the scope of the present invention. The ability to ascertain substantial identities of these patterns is within the purview of one of ordinary skill in the art.

Utility:

Crystalline forms of Compound (I), its salts and solvates, alone or in combination with other compounds, can be used to treat AIDS and/or HIV infection.

The crystalline forms of the invention may be formulated with one or more excipients or other materials to provide formulations suitable for the treatment of the indications identified above.

The crystalline forms of the present invention may be administered by various routes, and can be dissolved in various solvents prior to administration.

In accordance with the present invention there is further provided a method of treating and a pharmaceutical composition for treating viral infections such as HIV infection and AIDS. The treatment involves administering to a patient in need of such treatment a pharmaceutical composition comprising a pharmaceutical carrier and a therapeutically-effective amount of a crystalline form of the present disclosure.

The pharmaceutical composition may be in the form of orally-administrable suspensions or tablets; nasal sprays, sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

Compound (I) may be present in the novel crystalline forms as the neat form, solvate and/or hydrate. A wide variety of solvents may be employed in the preparation of the solvates of Compound (I). Preferred solvents include, for example, polar solvents, including polar protic and polar aprotic solvents. In preferred form, the solvent employed in the preparation include, for example, DMF or acetone, preferably acetone. The ratio of Compound (I) to solvent in the solvates may vary and depends, for example, on the particular solvent selected and the methods for preparing the solvates. Preferably, the solvates are monosolvates, hemisolvates, non-stoichiometric or disolvates.

Abbreviations

The following abbreviations, most of which are conventional abbreviations well known to those skilled in the art, are used throughout the description of the invention and the examples. Some of the abbreviations used are as follows:

h=hour(s)
rt=room temperature
mol=mole(s)
mmol=millimole(s)
g=gram(s)
mg=milligram(s)
mL=milliliter(s)
TFA=Trifluoroacetic Acid
DCE=1,2-Dichloroethane
$CH_2Cl_2$=Dichloromethane
TPAP=tetrapropylammonium perruthenate
THF=Tetrahydofuran
DEPBT=3-(Diethoxyphosphoryloxy)-1,2,3-benzotriazin-4(3H)-one
DMAP=4-dimethylaminopyridine
P-EDC=Polymer supported 1-(3-dimethylaminopropyl)-3-ethylcarbodiimide
EDC=1-(3-dimethylaminopropyl)-3-ethylcarbodiimide
DMF=N,N-dimethylformamide
Hunig's Base=N,N-Diisopropylethylamine
mCPBA=meta-Chloroperbenzoic Acid
azaindole=1H-Pyrrolo-pyridine
4-azaindole=1H-pyrrolo[3,2-b]pyridine
5-azaindole=1H-Pyrrolo[3,2-c]pyridine
6-azaindole=1H-pyrrolo[2,3-c]pyridine
7-azaindole=1H-Pyrrolo[2,3-b]pyridine
PMB=4-Methoxybenzyl
DDQ=2,3-Dichloro-5,6-dicyano-1,4-benzoquinone
OTf=Trifluoromethanesulfonoxy
NMM=4-Methylmorpholine
PIP-COPh=1-Benzoylpiperazine
NaHMDS=Sodium hexamethyldisilazide
EDAC=1-(3-Dimethylaminopropyl)-3-ethylcarbodiimide
TMS=Trimethylsilyl
DCM=Dichloromethane
DCE=Dichloroethane
MeOH=Methanol
THF=Tetrahrdrofuran
EtOAc=Ethyl Acetate
LDA=Lithium diisopropylamide
TMP-Li=2,2,6,6-tetramethylpiperidinyl lithium
DME=Dimethoxyethane
DIBALH=Diisobutylaluminum hydride
HOBT=1-hydroxybenzotriazole
CBZ=Benzyloxycarbonyl
PCC=Pyridinium chlorochromate
Me=Methyl
Ph=Phenyl The crystalline materials of Compound (I) described herein may be formulated into pharmaceutical compositions and/or employed in therapeutic and/or prophylactic methods. These methods include, but are not limited to, the administration of the crystalline compound (I), alone or in combination with one or more other pharmaceutically active agents, including agents that may be useful in the treatment of the disorders mentioned herein.

The methods preferably comprise administering to a patient a pharmaceutically effective amount of the novel crystals of the present invention, preferably in combination with one or more pharmaceutically acceptable carriers and/or excipients. The relative proportions of active ingredient and carrier and/or excipient may be determined, for example, by the solubility and chemical nature of the materials, chosen route of administration and standard pharmaceutical practice.

The crystalline forms of Compound (I) may be administered to a patient in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They may be administered alone, but generally will be administered with a pharmaceutical carrier selected on the basis of the chosen route of administration and standard pharmaceutical practice.

The dosage regimen for the crystalline forms of Compound (I) will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder. Obviously, several unit dosage forms may be administered at about the same time. The dosage of the crystalline form of Compound (I) that will be most suitable for prophylaxis or treatment may vary with the form of administration, the particular crystalline form of the compound chosen and the physiological characteristics of the particular patient under treatment. Broadly, small dosages may be used initially and, if necessary, increased by small increments until the desired effect under the circumstances is reached.

By way of general guidance, in the adult, suitable doses may range from about 0.001 to about 1000 mg/Kg body weight, and all combinations and subcombinations of ranges and specific doses therein. Preferred doses may be from about 0.01 to about 100 mg/kg body weight per day by inhalation, preferably 0.1 to 70, more preferably 0.5 to 20 mg/Kg body weight per day by oral administration, and from about 0.01 to about 50, preferably 0.01 to 10 mg/Kg body weight per day by intravenous administration. In each particular case, the doses may be determined in accordance with the factors distinctive to the subject to be treated, such as age, weight, general state of health and other characteristics which can influence the efficacy of the medicinal product. The crystalline forms of Compound (I) may be administered in a single daily dose, or the total daily dosage may be administered in divided doses of two, three, or four times daily.

For oral administration in solid form such as a tablet or capsule, the crystalline forms of Compound (I) can be combined with a non-toxic, pharmaceutically acceptable inert carrier, such as lactose, starch, sucrose, glucose, methylcellulose, magnesium stearate, dicalcium phosphate, calcium sulfate, mannitol, sorbitol and the like.

Preferably, in addition to the active ingredient, solid dosage forms may contain a number of additional ingredients referred to herein as "excipients". These excipients include among others diluents, binders, lubricants, glidants and disintegrants. Coloring agents may also be incorporated. "Diluents", as used herein, are agents which impart bulk to the formulation to make a tablet a practical size for compression. Examples of diluents are lactose and cellulose. "Binders", as used herein, are agents used to impart cohesive qualities to the powered material to help ensure the tablet will remain intact after compression, as well as improving the free-flowing qualities of the powder. Examples of typical binders are lactose, starch and various sugars. "Lubricants", as used herein, have several functions including preventing the adhesion of the tablets to the compression equipment and improving the flow of the granulation prior to compression or encapsulation. Lubricants are in most cases hydrophobic materials. Excessive use of lubricants is undesired, however, as it may result in a formulation with reduced disintegration and/or delayed dissolution of the drug substance. "Glidants", as used herein, refer to substances which may improve the flow characteristics of the granulation material. Examples of glidants include talc and colloidal silicon dioxide. "Disintegrants", as used herein, are substances or a mixture of substances added to a formulation to facilitate the breakup or disintegration of the solid dosage form after administration. Materials that may serve as disintegrants include starches, clays, celluloses, algins, gums and cross-linked polymers. A group of disintegrants referred to as "super-disintegrants" generally are used at a low level in the solid dosage form, typically 1% to 10% by weight relative to the total weight of the dosage unit. Croscarmelose, crospovidone and sodium starch glycolate represent examples of a cross-linked cellulose, a cross-linked polymer and a cross-linked starch, respectively. Sodium starch glycolate swells seven- to twelve-fold in less than 30 seconds effectively disintegrating the granulations that contain it.

The disintegrant preferably used in the present invention is selected from the group comprising modified starches, croscarmallose sodium, carboxymethylcellulose calcium and crospovidone. A more preferred disintegrant in the present invention is a modified starch such as sodium starch glycolate.

Preferred carriers include capsules or compressed tablets which contain the solid pharmaceutical dosage forms described herein. Preferred capsule or compressed tablet forms generally comprise a therapeutically effective amount of the crystalline forms of Compound (I) and one or more disintegrants in an amount greater than about 10% by weight relative to the total weight of the contents of the capsule or the total weight of the tablet.

Preferred capsule formulations may contain the crystalline forms of Compound (I) in an amount from about 5 to about 1000 mg per capsule. Preferred compressed tablet formulations contain the crystalline forms of Compound (I) in an amount from about 5 mg to about 800 mg per tablet. More preferred formulations contain about 50 to about 200 mg per capsule or compressed tablet. Preferably, the capsule or compressed tablet pharmaceutical dosage form comprises a therapeutically effective amount of a crystalline form of Compound (I); a surfactant; a disintegrant; a binder; a lubricant; and optionally additional pharmaceutically acceptable excipients such as diluents, glidants and the like; wherein the disintegrant is selected from modified starches; croscarmallose sodium, carboxymethylcellulose calcium and crospovidone.

For oral administration in liquid form, the crystalline forms of Compound (I) can be combined with any oral, non-toxic pharmaceutically acceptable inert carrier such as ethanol, glycerol, water and the like. The liquid composition may contain a sweetening agent which to make the compositions more palatable. The sweetening agent can be selected from a sugar such as sucrose, mannitol, sorbitol, xylitol, lactose, etc. or a sugar substitute such as cyclamate, saccaharin, aspartame, etc. If sugar substitutes are selected as the sweetening agent the amount employed in the compositions of the invention will be substantially less than if sugars are employed. Taking this into account, the amount of sweetening agent may range from about 0.1 to about 50% by weight, and all combinations and subcombinations of ranges and specific amounts therein. Preferred amounts range from about 0.5 to about 30% by weight.

The more preferred sweetening agents are the sugars and particularly sucrose. The particle size of the powdered sucrose used has been found to have a significant influence in the physical appearance of the finished composition and its ultimate acceptance for taste. The preferred particle size of the sucrose component when used is in the range of from 200 to less than 325 mesh US Standard Screen, and all combinations and subcombinations of ranges and specific particle sizes therein.

Sterile injectable solutions may be prepared by incorporating the crystalline forms of Compound (I) in the required amounts, in the appropriate solvent, with various of the other ingredients enumerated herein, as required, followed by filtered sterilization. Generally, dispersions may be prepared by incorporating the sterilized active ingredient into a sterile vehicle which contains the dispersion medium and any other required ingredients. In the case of sterile powders for the preparation of sterile injectable solutions, the preferred methods of preparation may include vacuum drying and the freeze drying technique which may yield a powder of the active ingredient, plus any additional desired ingredient from the previously sterile-filtered solution thereof.

As would be apparent to a person of ordinary skill in the art, once armed with the teachings of the present disclosure, when dissolved, Compound (I) loses its crystalline structure, and is therefore considered to be a solution of Compound (I). All forms of the present invention, however, may be used for the preparation of liquid formulations in which Compound (I) may be, for example, dissolved or suspended. In addition, the crystalline forms of Compound (I) may be incorporated into solid formulations.

The liquid compositions may also contain other components routinely utilized in formulating pharmaceutical compositions. One example of such components is lecithin. Its use in compositions of the invention as an emulsifying agent in the range of from 0.05 to 1% by weight, and all combinations and subcombinations of ranges and specific amounts therein. More preferably, emulsifying agents may be employed in an amount of from about 0.1 to about 0.5% by weight. Other examples of components that may be used are antimicrobial preservatives, such as benzoic acid or parabens; suspending agents, such as colloidal silicon dioxide; antioxidants; topical oral anesthetics; flavoring agents; and colorants.

The selection of such optional components and their level of use in the compositions of the invention is within the level of skill in the art and will be even better appreciated from the working examples provided hereinafter.

The crystalline forms of Compound (I) may also be coupled with soluble polymers as targetable drug carriers. Such polymers can include polyvinylpyrrolidine pyran copolymer, polyhydroxypropylmethacrylamide-phenol, polyhydroxyethyl-aspartamidephenol or polyethylene oxide-polylysine substituted with palmitolyl residues. Gelatin capsules of the crystalline forms of Compound (I) may contain the crystalline Compound (I) and the liquid or solid compositions described herein. Gelatin capsules may also contain powdered carriers such as lactose, starch, cellulose derivatives, magnesium stearate, stearic acid and the like. Similar diluents can be used to make compressed tablets. Both tablets and capsules can be manufactured as sustained release products to provide for continuous release of medication over a period of hours. Tablets can be sugar coated or film coated to mask any unpleasant taste and to protect the tablet from the atmosphere or enteric coated for selective disintegration in the gastrointestinal track.

In general, water, a suitable oil, saline, aqueous dextrose (glucose), and related sugar solutions and glycols, such as propylene glycol or polyethylene glycols are suitable carriers for parenteral solutions. Solutions for parenteral solutions are prepared by dissolving the crystalline Efavirenz in the carrier and, if necessary, adding buffering substances. Anti-oxidizing agents such as sodium bisulfite, sodium sulfite, or ascorbic acid either alone or combined, are suitable stabilizing agents. Citric acid and its salts and sodium EDTA may also be employed. Parenteral solutions may also contain preservatives, such as benzalkonium chloride, methyl- or propyl-paraben and chlorobutanol.

Suitable pharmaceutical carriers are described in Remington's Pharmaceutical Sciences, Mack Publishing Co., the disclosures of which are hereby incorporated herein by reference, in their entireties.

The preferred crystalline form of Compound (I) may serve as component (a) of this invention and can independently be in any dosage form, such as those described above, and can also be administered in various combinations, as described above. In the following description component (b) is to be understood to represent one or more agents as described herein suitable for combination therapy.

Pharmaceutical kits which may be useful for the treatment of various disorders, and which comprise a therapeutically effective amount of a pharmaceutical composition comprising a novel form of Compound (I) in one or more sterile containers, are also within the ambit of the present invention. The kits may further comprise conventional pharmaceutical kit components which will be readily apparent to those skilled in the art, once armed with the present disclosure. Sterilization of the container may be carried out using conventional sterilization methodology well known to those skilled in the art.

Form N-2 (Free Acid)

Form N-2 is essentially free of water.

Form N-2 has the molecular formula of

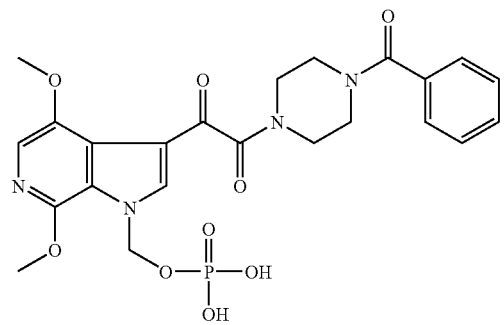

The single crystal of Form N-2 can be characterized as follows:

| | |
|---|---|
| Temperature | 293(2) K |
| Wavelength | 1.54178 A |
| Crystal system, space group | Monoclinic, P2(1)/c |
| Unit cell dimensions | a = 12.922(2) A |
| | alpha = 90 deg. |
| | b = 10.7438(18) A |
| | beta = 101.002(4) deg. |
| | c = 17.803(3) A |
| | gamma = 90 deg. |
| Volume | 2426.3(7) A^3 |
| Z, Calculated density | 4, 1.458 Mg/m^3 |
| Crystal size | 0.14 × 0.04 × 0.03 mm |

Figure 4:
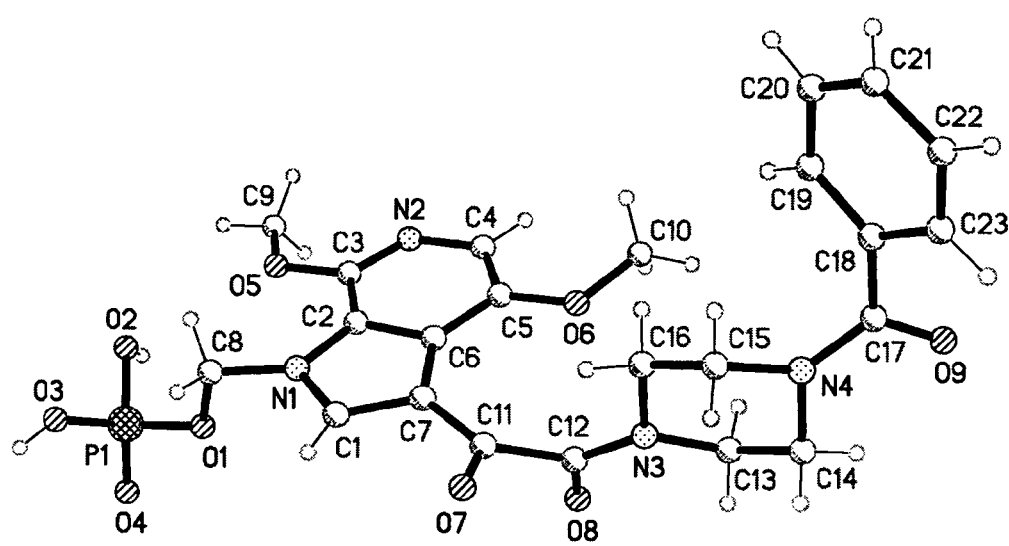
FIG. 4. illustrates the labeling of atoms (except H atoms) in Form N-2 of Compound (I).

Each of the atoms (except H) in Form N-2 is labeled according to FIG. 4. The fractional atomic coordinates of are listed in Table 1.

From N2 can be obtained from the reaction of phosphoric acid, [3-[2-(4-benzoyl-1-piperazinyl)-1,2-dioxoethyl]-4,7-dimethoxy-1H-pyrrolo[2,3-c]pyridin-1-yl]methyl bis(1,1-dimethylethyl) ester with TFA or some other acid in a suitable solvent such as DCM. After solvent swap to a suitable crystallization solvent such as MeOH, EtOH, or IPA, the N2 form can be obtained. After filtration, the wet cake should be dried at temperatures lower than 50° C. to ensure that the bound water is not removed To form single crystal of Form N-2, the dry cake was recrystallized from MeOH/CH$_2$Cl$_2$.

The N2 form can also be obtained from the H1 form by slurrying in MeOH, EtOH or IPA under ambient conditions for an extended period of time Form H-1 (Free Acid)

The stoichiometric ratio for Form H-1 Free Acid is Compound (I):Water=about 1:1.

Form H-1 has the molecular formula of

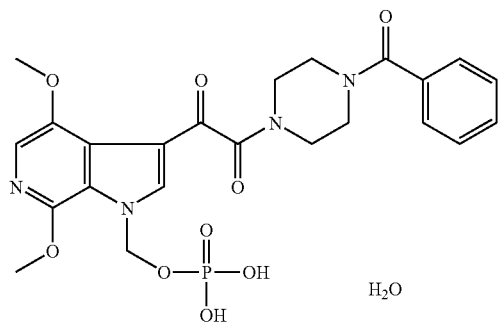

The single crystal of Form H-1 can be characterized as follows:

| | |
|---|---|
| Temperature | 293(2) K |
| Wavelength | 1.54178 A |
| Crystal system, space group | Triclinic, P-1 |
| Unit cell dimensions | a = 6.9238(4) A |
| | alpha = 80.074(2) deg. |
| | b = 13.4819(6) A |
| | beta = 87.292(3) deg. |
| | c = 13.5081(7) A |
| | gamma = 81.058(3) deg. |
| Volume | 1226.69(11) A^3 |
| Z, Calculated density | 2, 1.490 Mg/m^3 |
| Absorption coefficient | 1.581 mm^−1 |
| F(000) | 576 |
| Crystal size | 0.40 × 0.03 × 0.01 mm |
| Theta range for data collection | 3.32 to 60.32 deg. |

Figure 9:
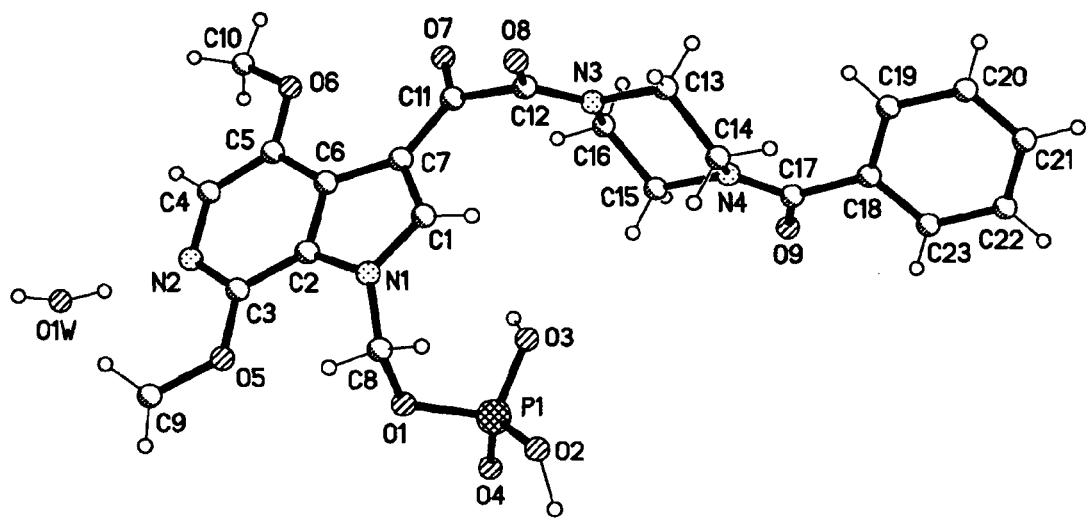
FIG. 9. illustrates the labeling of atoms (except H atoms) in Form H-1 of Compound (I).
Figure 10:
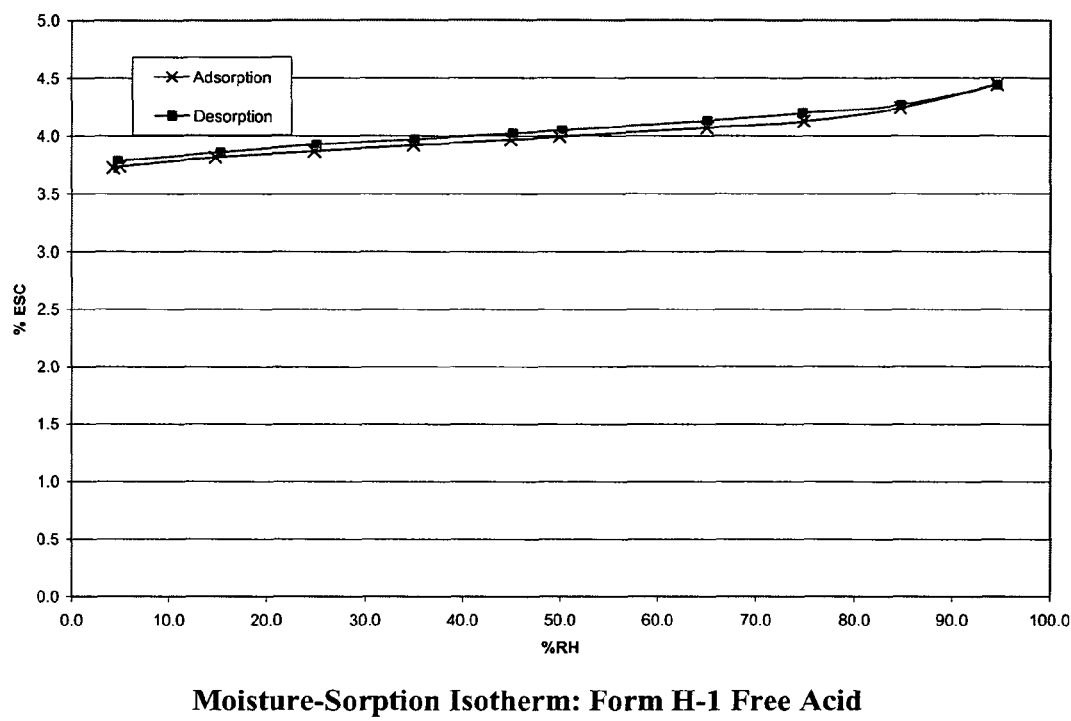
FIG. 10 illustrates moisture-sorption isotherms of Form H-1 of Compound (I).
Figure 11:
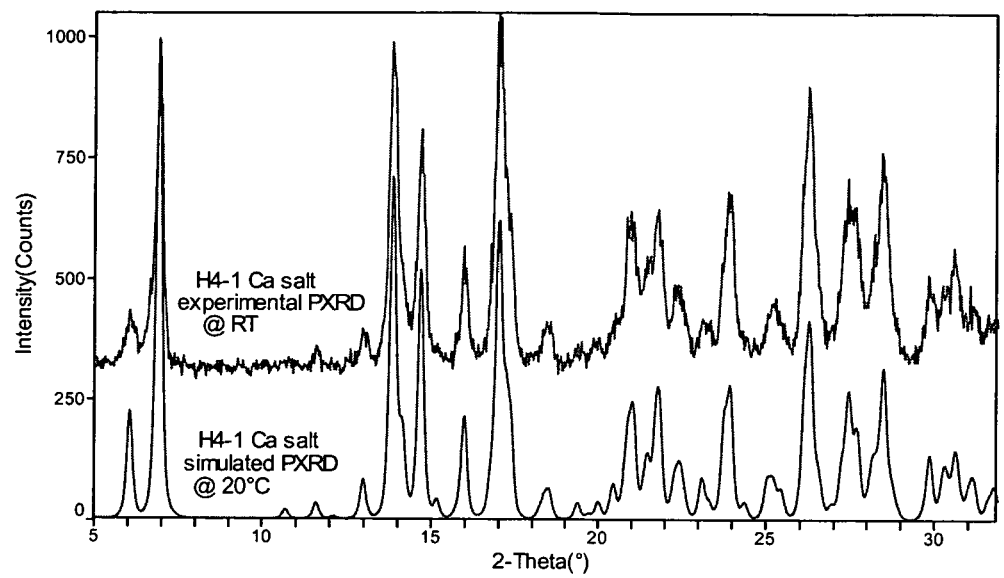
FIG. 11. illustrates experimental and simulated powdered X-ray diffraction patterns of Form Hemi-Calcium Salt H4-1 of Compound (I).
Figure 12:
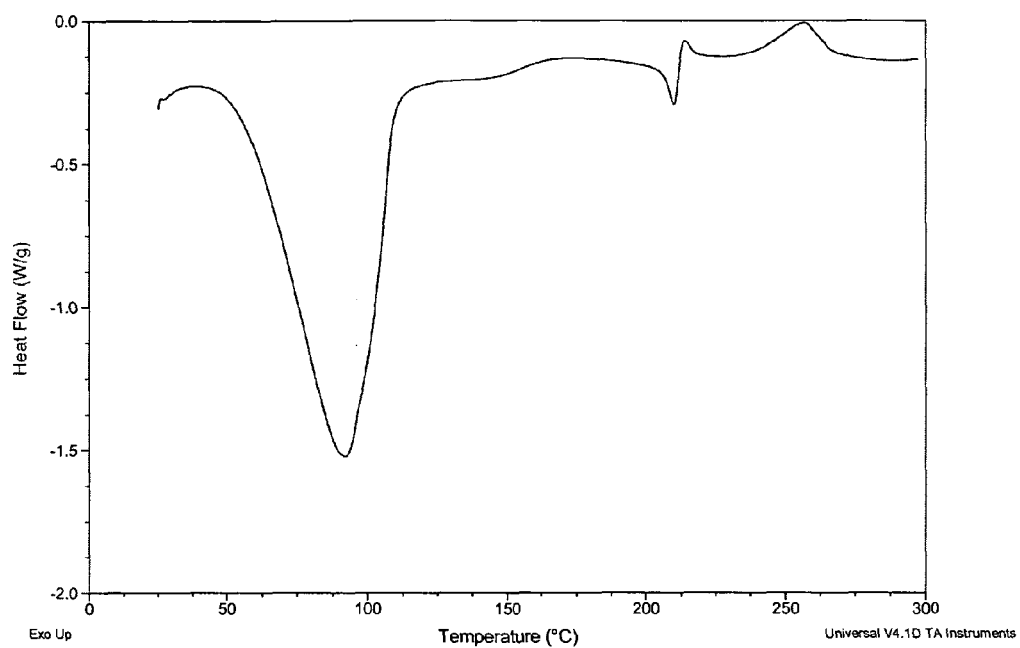
FIG. 12. illustrates differential scanning calorimetry pattern of Form Hemi-Calcium Salt H4-1 of Compound (I).
Figure 13:
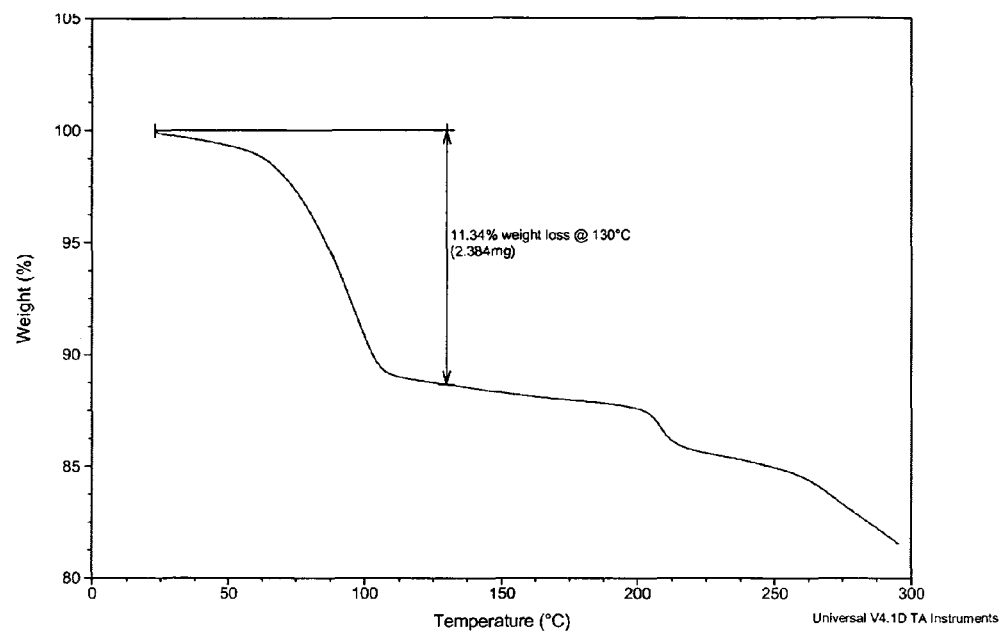
FIG. 13. illustrates thermogravimetric analysis pattern of Form Hemi-Calcium Salt H4-1 of Compound (I).

Each of the atoms (except H) in Form H-1 is labeled according to FIG. 9. The fractional atomic coordinates are listed in Table 2.

Form H-1 can be obtained from Form N-2, or a mixture of N-2 and H-1, by recrystallization in solvents containing water and another organic solvent. Examples of such organic solvents include ethanol, iso-propanol, tetrahydrofuran, acetonitrile, and acetone. The concentration of water in these solvents can range from 10 to 70% by volume. The ideal solvent is one that has a high solubility for the free acid at high temperature (say 70° C.) and a low solubility at room temperature. Then the acid can be easily solubilized at high temperature and recrystallized by cooling to room temperature. After filtration, the wet cake should be dried at temperatures lower than 50° C., and relative humidity greater than 2% to ensure that the bound water is not removed.

Form Hemi-Calcium Salt—H4-1

The stoichiometric ratio for Form Hemi-Calcium Salt H4-1 is Compound (I):Ca:water=about 1:0.5:4.

Form Hemi-Calcium Salt—H4-1 has the molecular formula of

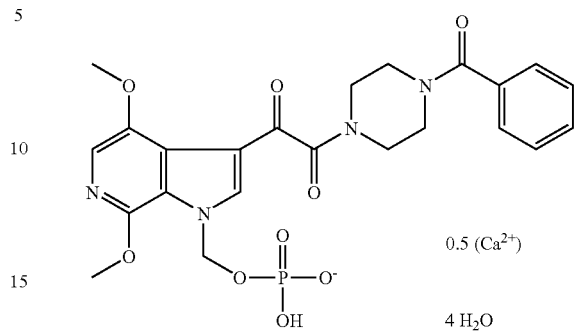

The single crystal of Form Hemi-Calcium Salt H4-1 can be characterized as follows:

| | |
|---|---|
| Temperature | 293(2) K |
| wavelength | 1.54178 A |
| Crystal system, space group | Triclinic, P-1 |
| Unit cell dimensions | a = 6.8710(1) A |
| | alpha = 68.675(1) deg. |
| | b = 13.7752(2) A |
| | beta = 84.403(1) deg. |
| | c = 15.7227(2) A |
| | gamma = 84.015(1) deg. |
| Volume | 1375.84(3) A^3 |
| Z, Calculated density | 2, 1.505 Mg/m^3 |
| Absorption coefficient | 2.364 mm^−1 |
| F(000) | 654 |
| Crystal size | 0.42 × 0.13 × 0.05 mm |
| Theta range for data collection | 3.02 to 65.14 deg. |

Figure 14:
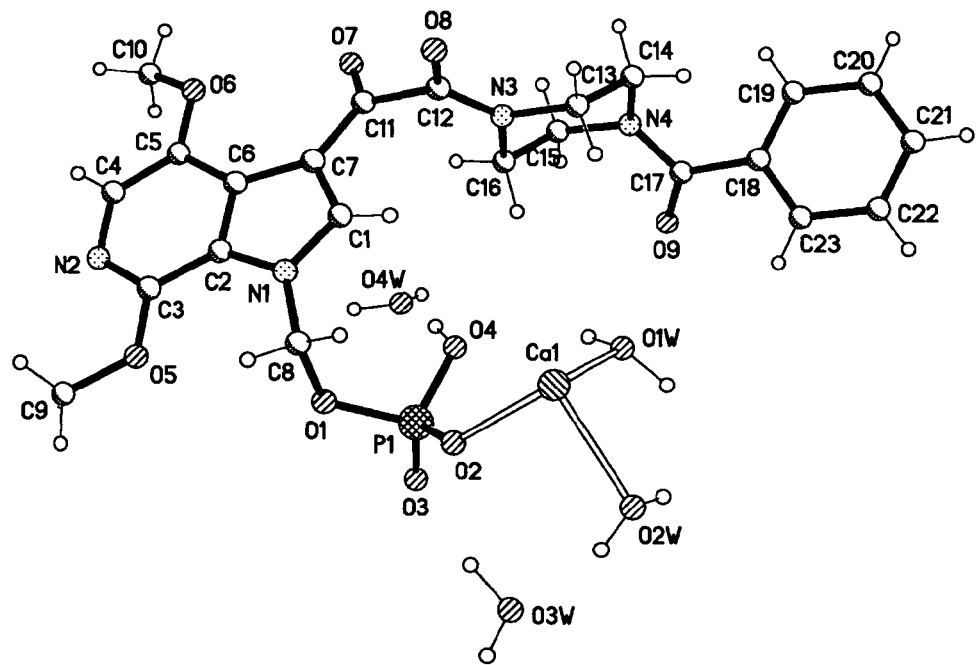
FIG. 14. illustrates the labeling of atoms (except H atoms) in Form Hemi-Calcium Salt H4-1 of Compound (I).
Figure 15:
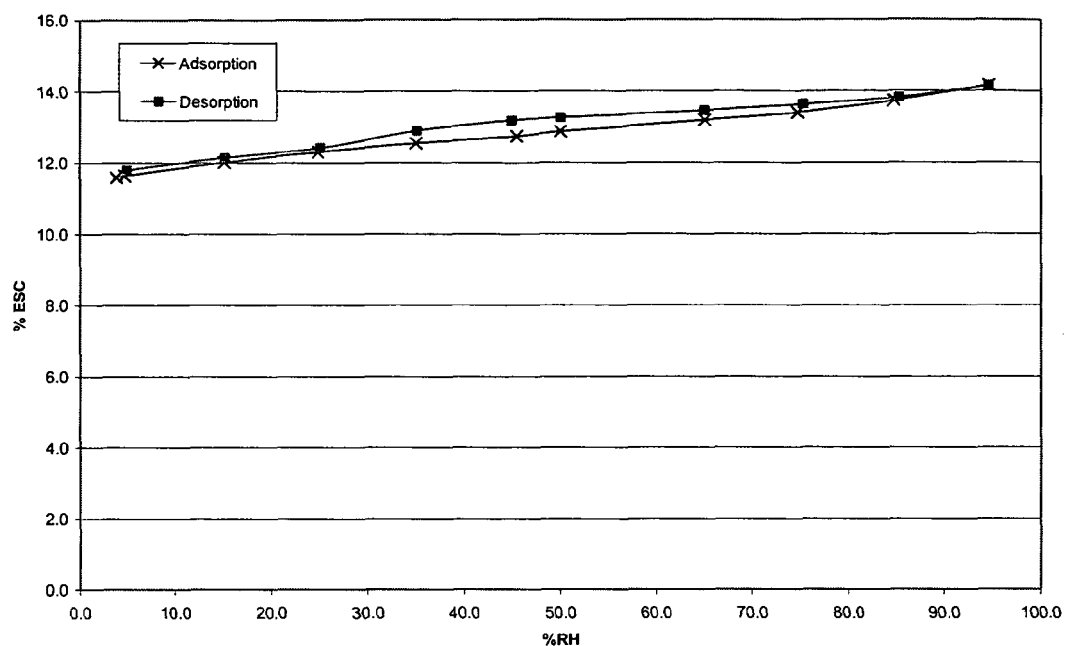
FIG. 15. illustrates moisture-sorption isotherms of Form Hemi-Calcium Salt H4-1 of Compound (I).
Figure 16:
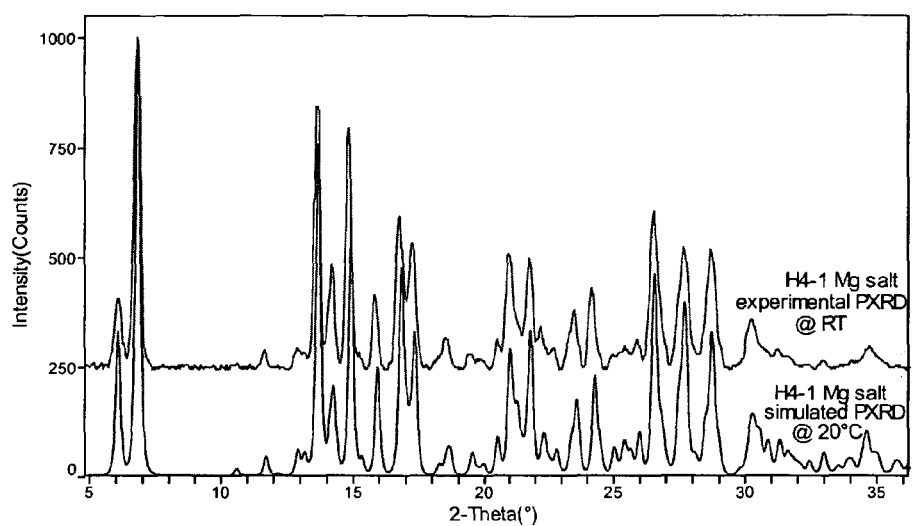
FIG. 16. illustrates experimental and simulated powdered X-ray diffraction patterns of Form Hemi-Magnesium Salt H4-1 of Compound (I).
Figure 17:
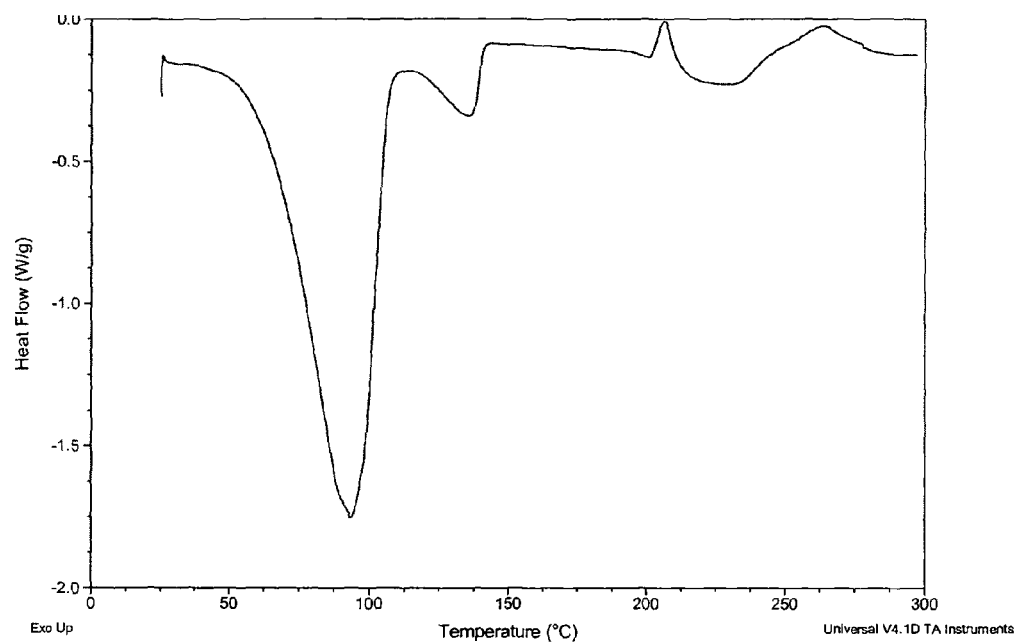
FIG. 17. illustrates differential scanning calorimetry pattern of Form Hemi-Magnesium Salt H4-1 of Compound (I).
Figure 18:
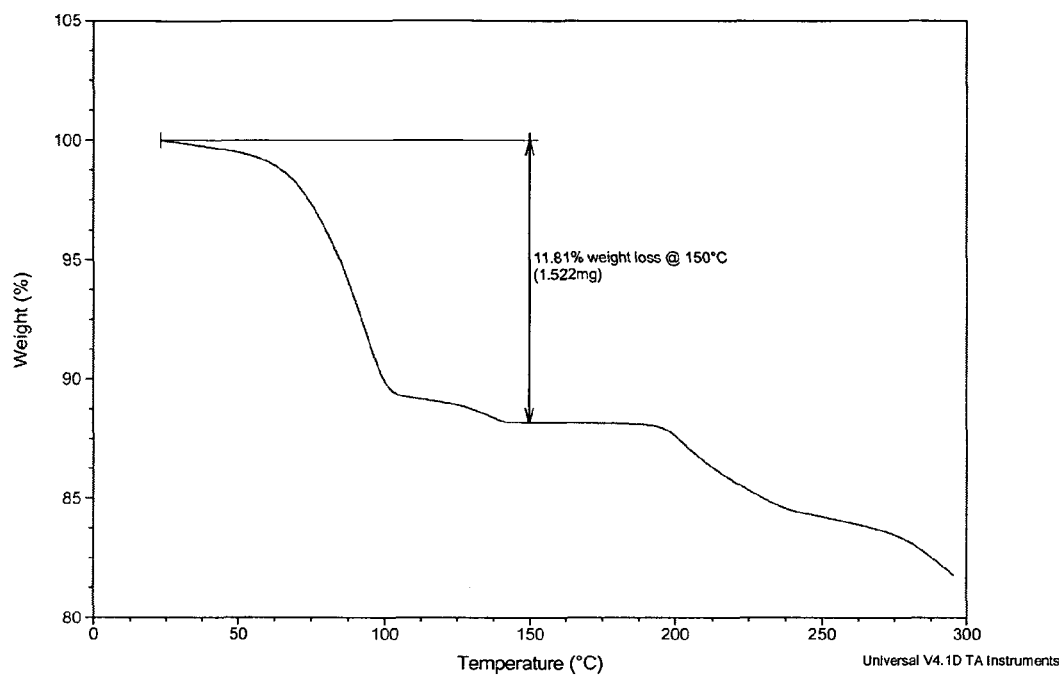
FIG. 18. illustrates thermogravimetric analysis pattern of Form Hemi-Magnesium Salt H4-1 of Compound (I).

Each of the atoms (except H) in Form Hemi-Calcium Salt-H4-1 is labeled according to FIG. 14. The atomic coordinates of are listed in Table 3.

Hemi-calcium salt H4-1 can be obtained by reaction of the free acid (N-2 or H-1) with a calcium base in water. Examples of such bases include calcium acetate and calcium methoxide. Although calcium hydroxide is an effective base, its low solubility in water hinders the reaction. Since the free acid is not very soluble in water, the completion of the reaction is obvious by the conversion of the free acid slurry to a clear yellow solution upon addition of the base (0.5 equivalent). Addition of seeds then results in gradual crystallization of H4-1. An alternate method to obtain H4-1 is by metathesis from another salt such as mono-lysine salt. In this case also the solvent is water, and the metathesis can be initiated by the addition of calcium salts such as calcium chloride, calcium sulfate, calcium acetate etc. After filtration, the wet cake of H4-1 can be dried under vacuum but the temperature should be below 35° C. and the relative humidity above 5% to ensure that the bound water is not lost.

Form Hemi-Magnesium Salt—H4-1

Form Hemi-Magnesium Salt-H4-1 has the molecular formula of

[Chemical structure showing the compound with 0.5 (Mg$^{2+}$) and 4 H$_2$O]

The stoichiometric ratio for Form is Compound (I):Mg:water=about 1:0.5:4.

The single crystal of Form Hemi-Magnesium Salt H4-1 can be characterized as follows:

| | |
|---|---|
| Temperature | 293(2) K |
| Wavelength | 1.54178 Å |
| Crystal system, space group | Triclinic, P-1 |
| Unit cell dimensions | a = 6.8710(1) Å |
| | alpha = 68.675(1) deg. |
| | b = 13.7752(2) Å |
| | beta = 84.403(1) deg. |
| | c = 15.7227(2) Å |
| | gamma = 84.015(1) deg. |
| Volume | 1375.84(3) Å$^3$ |
| Z, Calculated density | 2, 1.505 Mg/m$^3$ |
| Absorption coefficient | 2.364 mm$^{-1}$ |
| F(000) | 654 |
| Crystal size | 0.42 × 0.13 × 0.05 mm |
| Theta range for data collection | 3.02 to 65.14 deg. |

Figure 19:
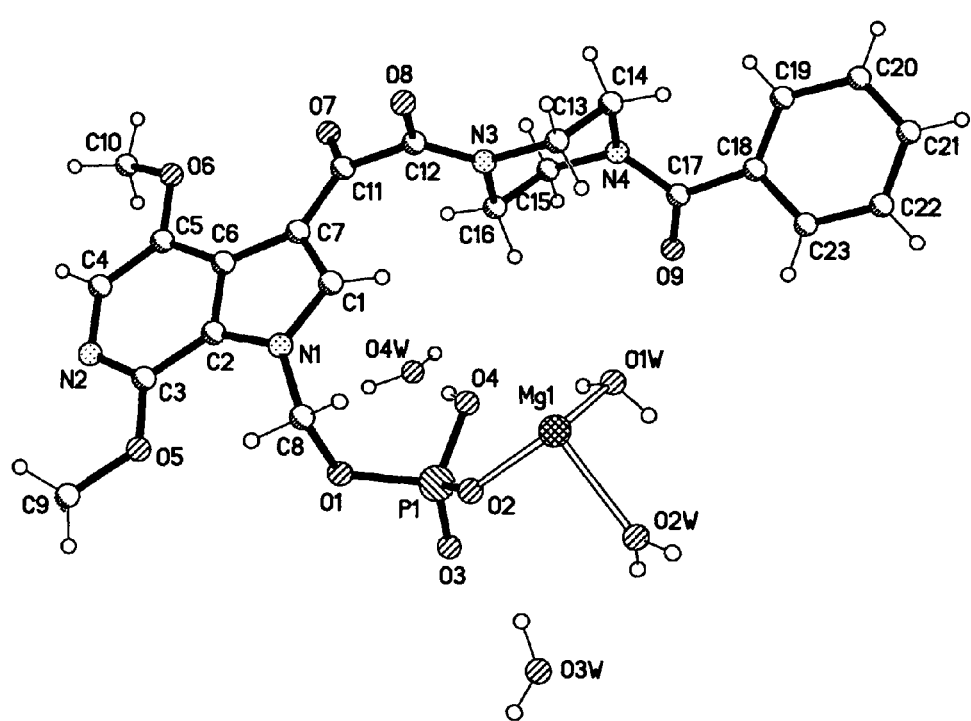
FIG. 19. illustrates the labeling of atoms (except H atoms) in Form Hemi-Magnesium Salt H4-1 of Compound (I).
Figure 20:
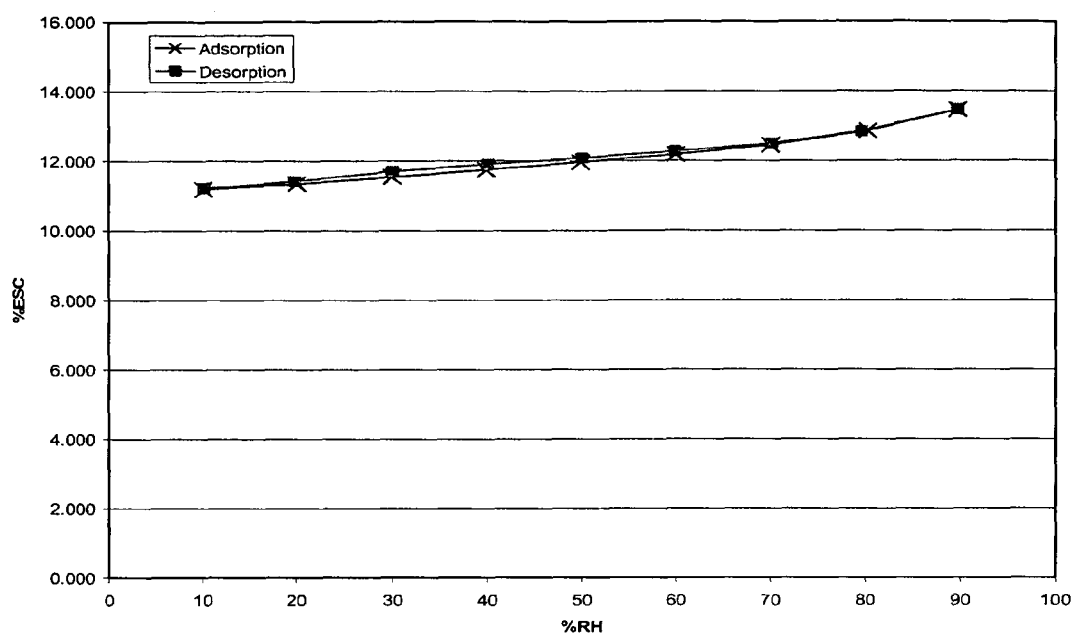
FIG. 20. illustrates moisture-sorption isotherms of Form Hemi-Magnesium Salt H4-1 of Compound (I).
Figure 21:
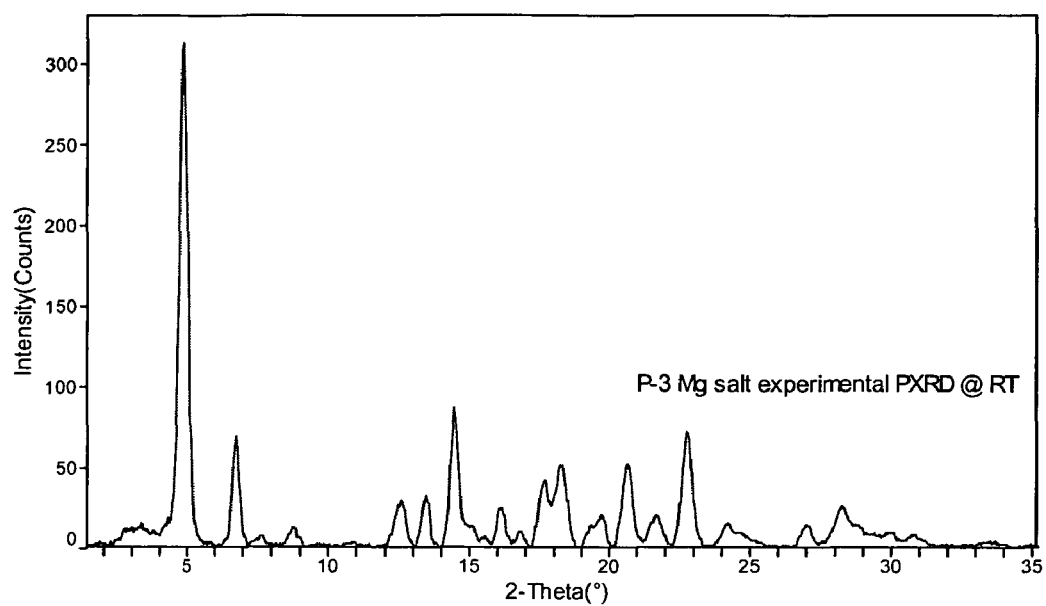
FIG. 21. illustrates experimental powdered X-ray diffraction patterns of Form Mono-Magnesium Salt P-3 of Compound (I).
Figure 22:
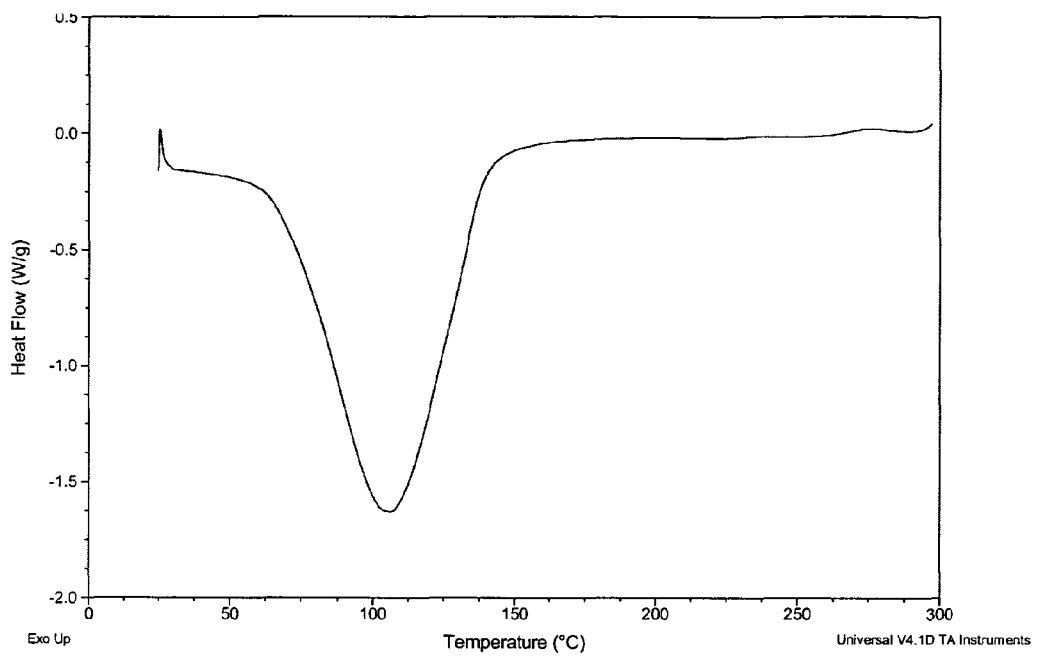
FIG. 22. illustrates differential scanning calorimetry pattern of Form Mono-Magnesium Salt P-3 of Compound (I).
Figure 23:
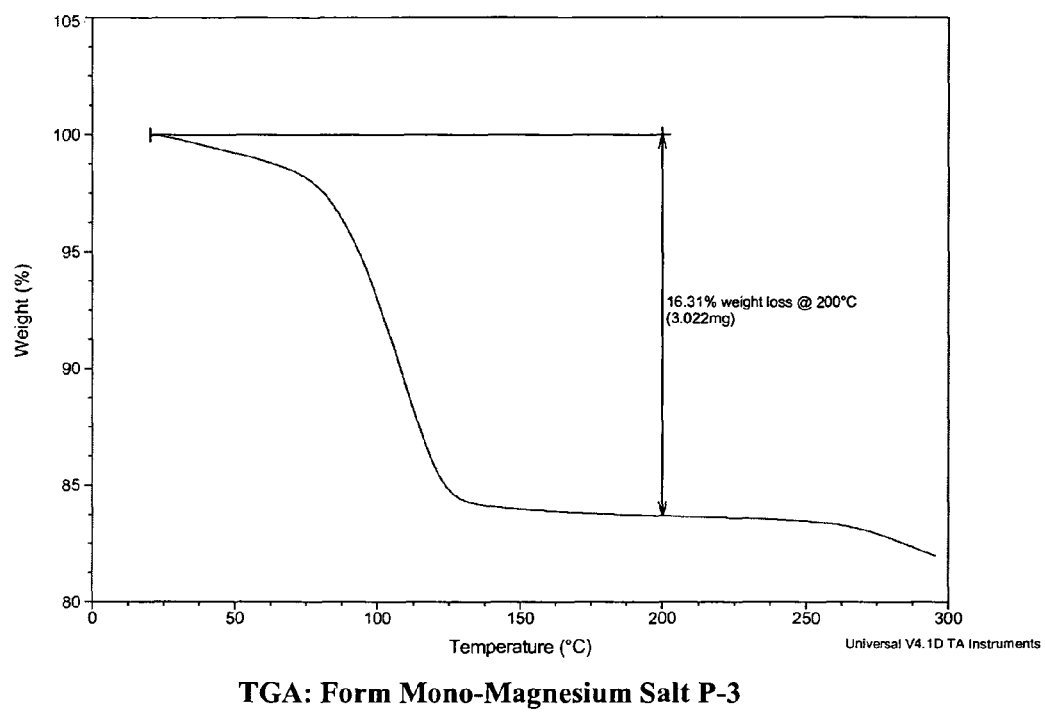
FIG. 23. illustrates thermogravimetric analysis pattern of Form Mono-Magnesium Salt P-3 of Compound (I).
Figure 24:
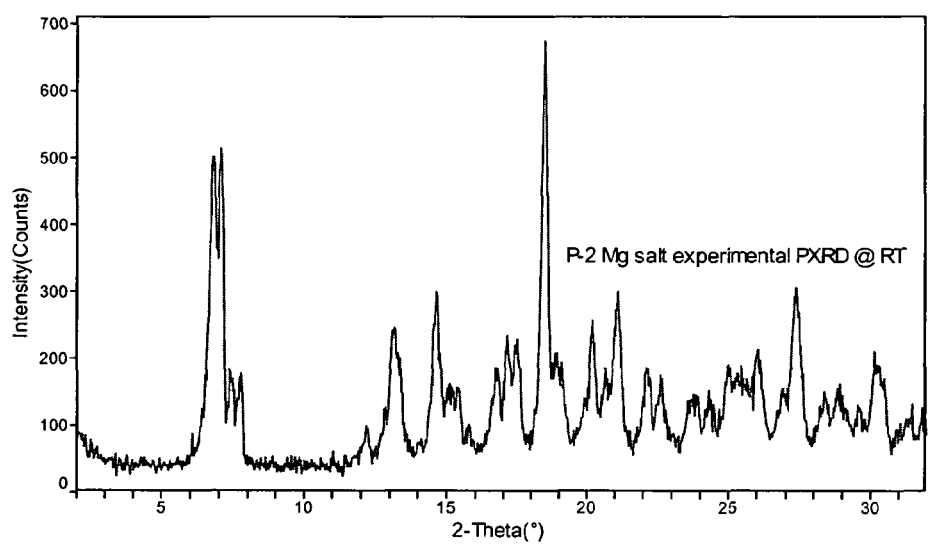
FIG. 24. illustrates experimental powdered X-ray diffraction patterns of Form Hemi-Magnesium Salt P-2 of Compound (I).
Figure 25:
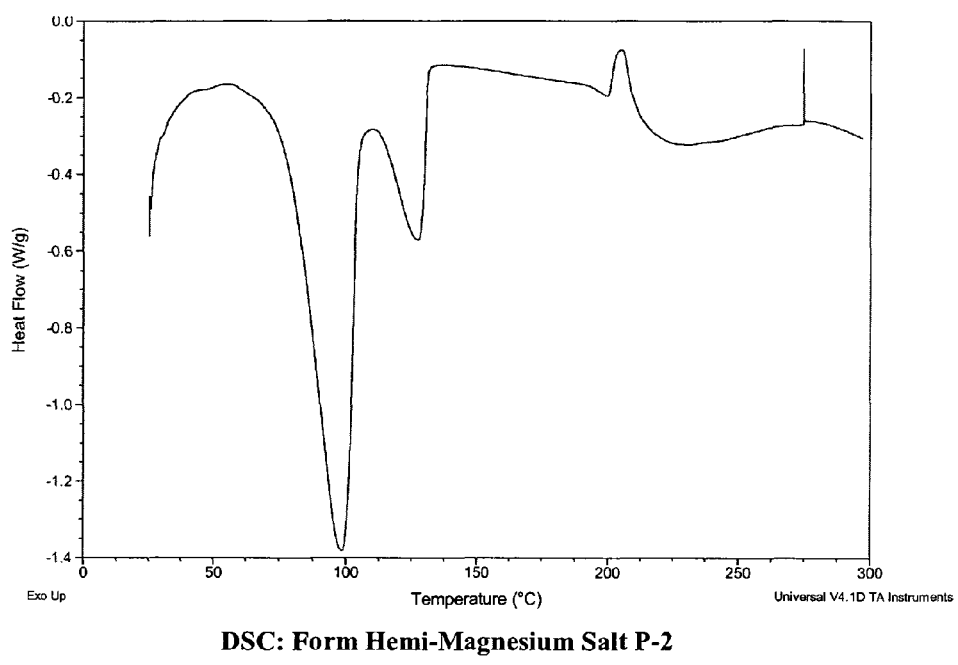
FIG. 25. illustrates differential scanning calorimetry pattern of Form Hemi-Magnesium Salt P-2 of Compound (I).
Figure 26:
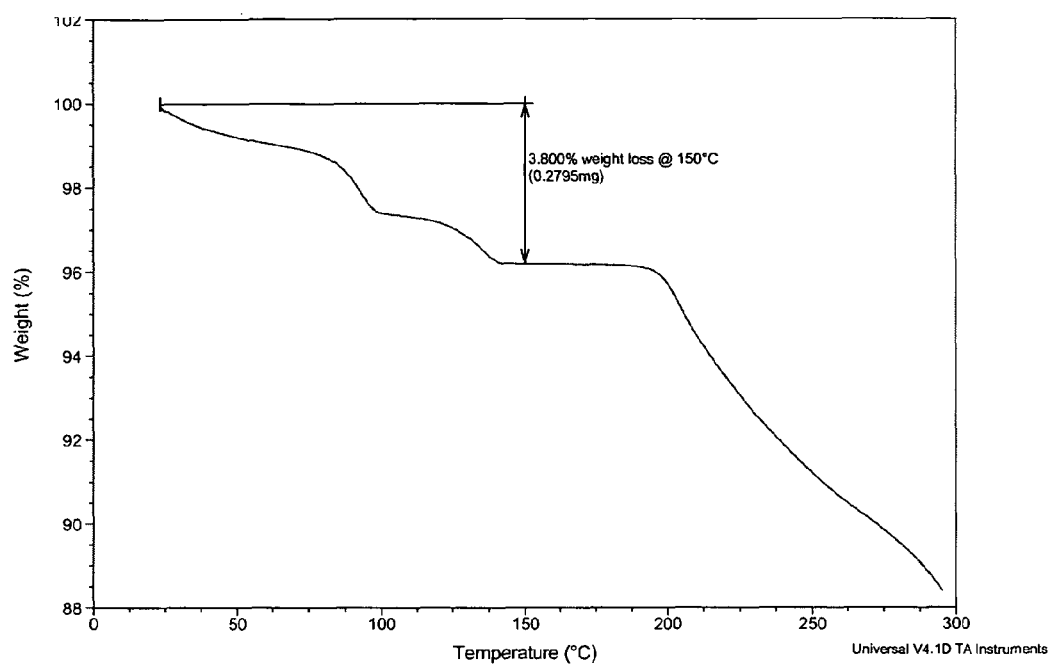
FIG. 26. illustrates thermogravimetric analysis pattern of Form Hemi-Magnesium Salt P-2 of Compound (I).
Figure 27:
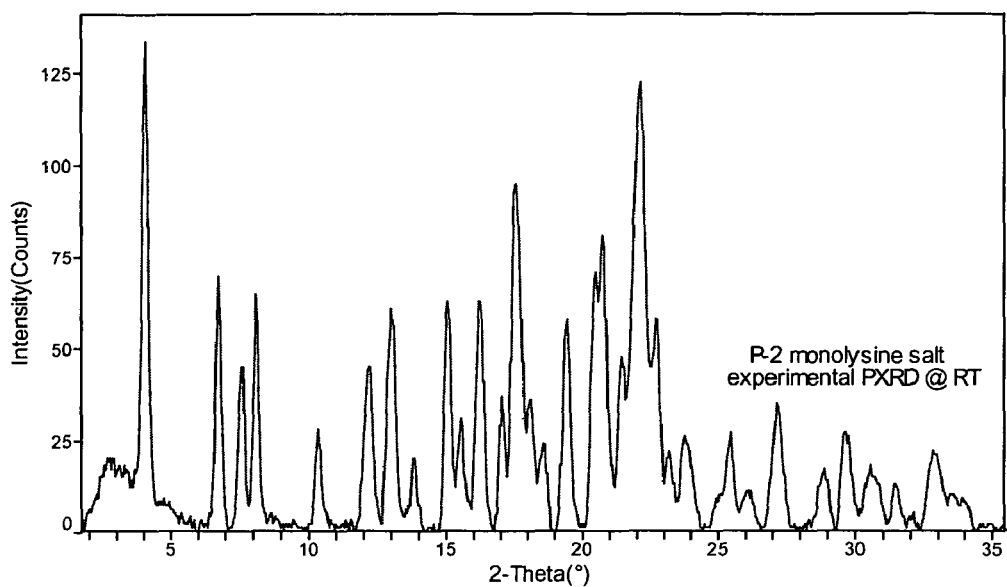
FIG. 27. illustrates experimental powdered X-ray diffraction patterns of Form Mono-Lysine Salt P-2 of Compound (I).
Figure 28:
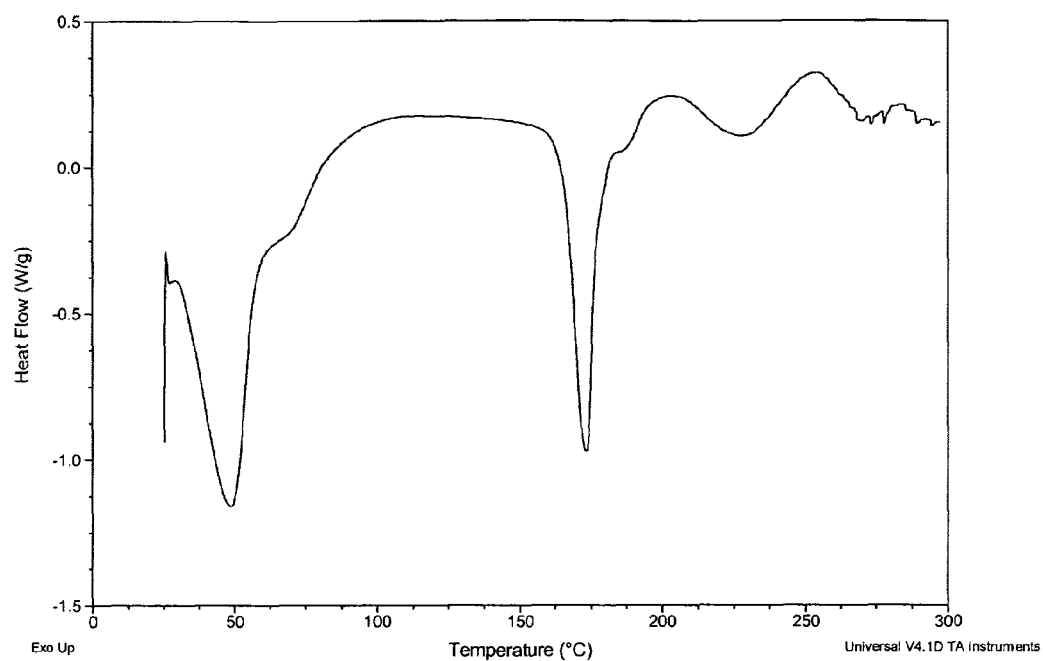
FIG. 28. illustrates differential scanning calorimetry pattern of Form Mono-Lysine Salt P-2 of Compound (I).
Figure 29:
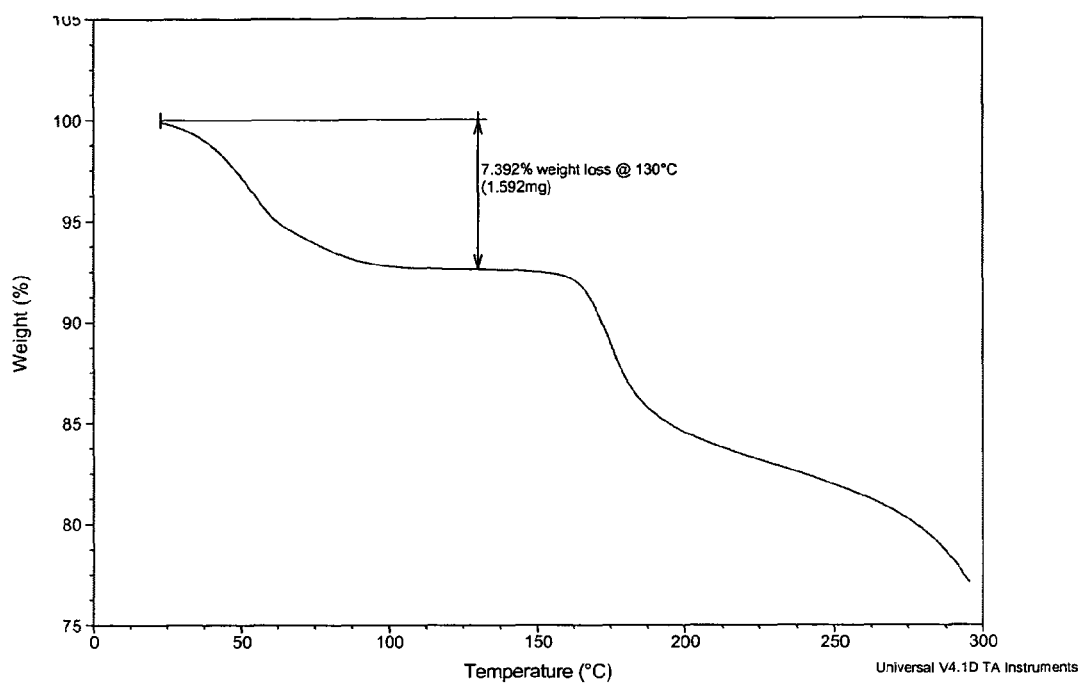
FIG. 29. illustrates thermogravimetric analysis pattern of Form Mono-Lysine Salt P-2 of Compound (I).
Figure 30:
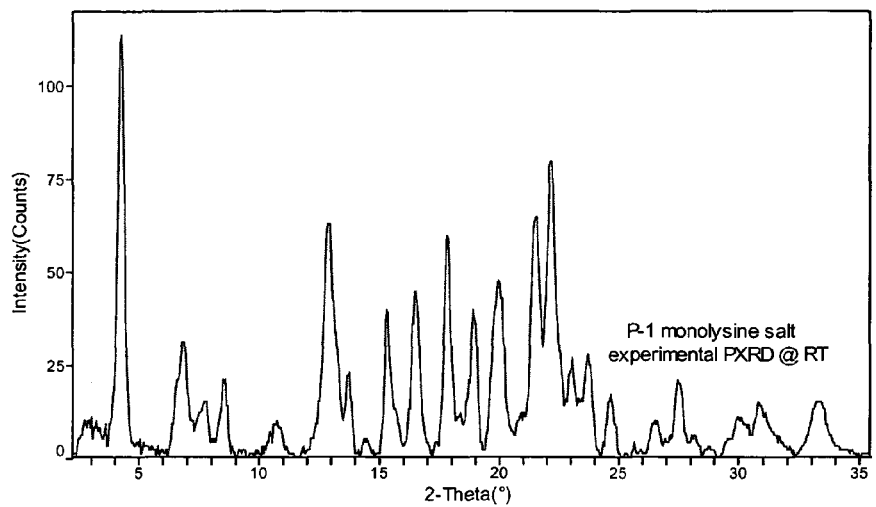
FIG. 30. illustrates experimental powdered X-ray diffraction patterns of Form Mono-Lysine Salt P-1 of Compound (I).
Figure 31:
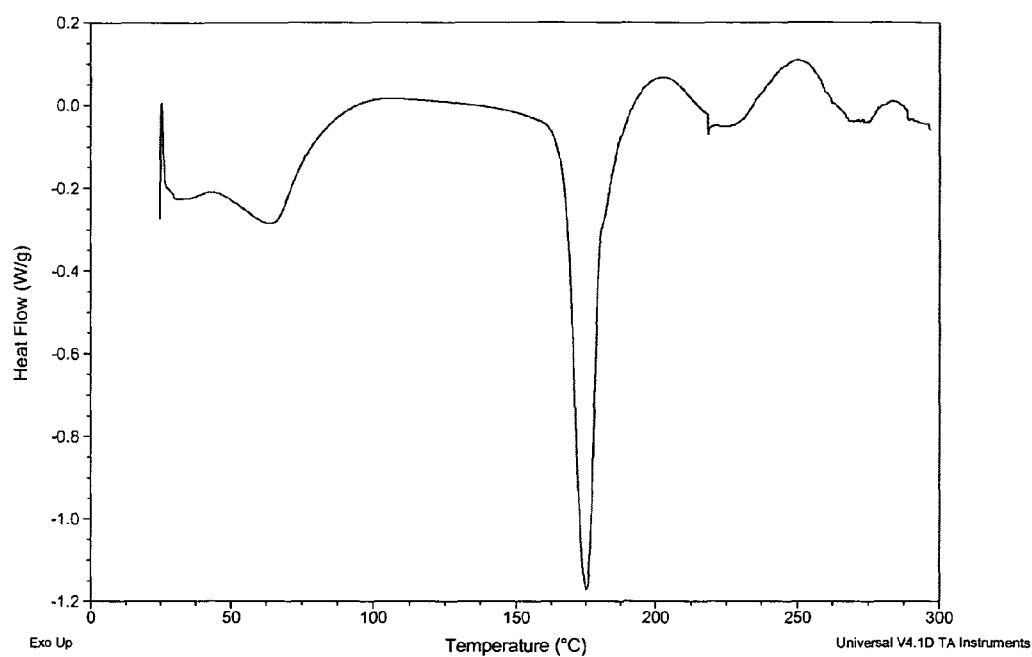
FIG. 31. illustrates differential scanning calorimetry pattern of Form Mono-Lysine Salt P-1 of Compound (I).
Figure 32:
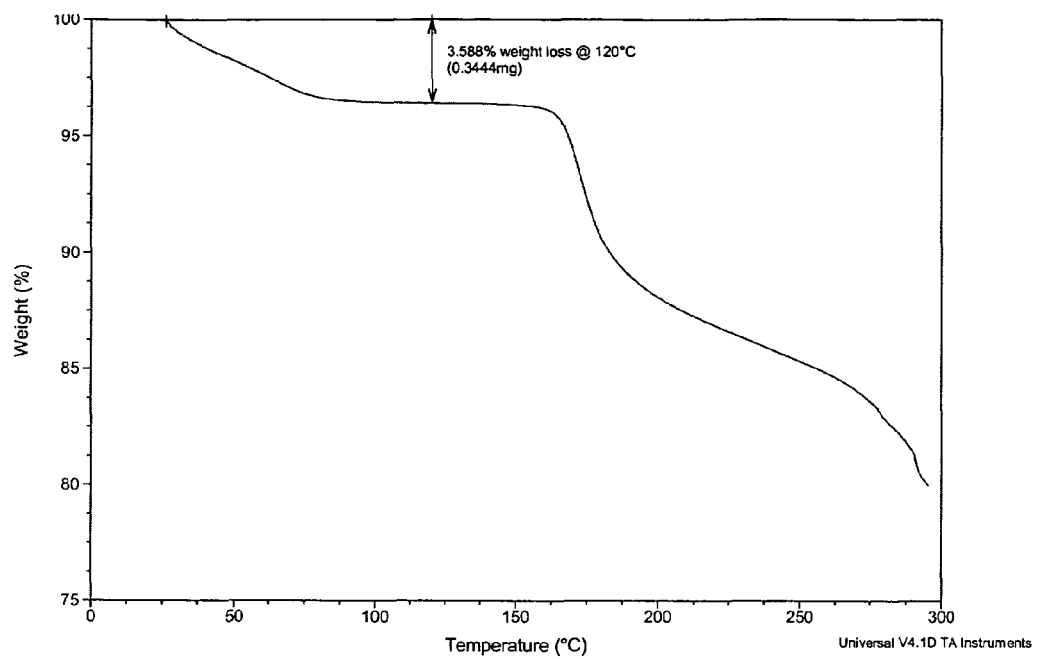
FIG. 32. illustrates thermogravimetric analysis pattern of Form Mono-Lysine Salt P-1 of Compound (I).

Each of the atoms (except H) in Form Hemi-Magnesium Salt-H4-1 is labeled according to FIG. 19. The fractional atomic coordinates of are listed in Table 4.

Hemi-magnesium salt H4-1 can be obtained by reaction of the free acid (N-2 or H-1) with 0.5 equivalent magnesium base in water. Examples of such bases include magnesium acetate, magnesium hydroxide and magnesium ethoxide. The reaction occurs within a few minutes and is obvious by the conversion of the free acid slurry to a clear yellow solution. Addition of seeds then results in gradual crystallization of H4-1. An alternate method to obtain H4-1 is by metathesis from another salt such as mono-lysine salt. In this case also the solvent is water, and the metathesis can be initiated by the addition of magnesium salts such as magnesium chloride, magnesium sulfate, magnesium acetate etc. After filtration, the wet cake of H4-1 can be dried under vacuum but the temperature should be below 35° C. and the relative humidity above 5% to ensure that the bound water is not lost.

Form Mono-Magnesium Salt—P-3

The stoichiometric ratio for Form Mono-Magnesium Salt P-3 is Compound (I):Mg=about 1:1.

Mono-magnesium salt P-3 can be obtained by reaction of the free acid (N-2 or H-1) with one equivalent of a strong magnesium base in water. Magnesium ethoxide was found to be the most effective base, while magnesium acetate and magnesium hydroxide were not as effective in converting the free acid to P-3. Once the acid and base have reacted, the reaction mixture turns clear yellow. Addition of seeds then results in gradual crystallization of P-3. After filtration, the wet cake of P-3 can be dried under vacuum but the temperature should be below 35° C. and the relative humidity above 5% to ensure that the bound water is not lost.

Form Hemi-Magnesium Salt—P-2

The stoichiometric ratio for Form Hemi-Magnesium Salt P-2 is Compound (I):Mg=about 1:0.5.

Hemi-Magnesium Salt P-2 is obtained by first forming hemi-magnesium salt H4-1 during crystallization. Once the slurry of H4-1 has been filtered, the wet cake should be dried at 40° C. or higher at low relative humidity (less than 5%). Under these conditions, some of the bound water in H4-1 evaporates resulting in conversion to P-2.

Form Mono-Lysine Salt—P-2

The stoichiometric ratio for Form Mono-Lysine Salt P-2 is Compound (I):Lysine=about 1:1.

The Mono-Lysine Salt—P-2 can be formed from the reaction of either Form Free Acid—N-2 or Free Acid H-1 and Lysine in water. After addition of a suitable anti-solvent such as EtOH, IPA, of Acetone, the P-2 form can be obtained. The wet cake is typically dried at temperatures below 35° C. and relative humidity above 10%.

The P-2 form can be obtained from the P-1 form by rehydration at high relative humidity, say above 50% at ambient temperature.

Form Mono-Lysine Salt—P-1

The stoichiometric ratio for Form Mono-Lysine Salt P—I is Compound (I):Lysine=about 1:1.

Mono-lysine salt P-1 can be obtained from P-2 by drying P-2 under conditions that result in loss of some of the bound water e.g above 50° C. at low relative humidity (less than 5%). Partial loss of the bound water result in conversion of P-2 to P-1.

The present invention is further described in the following examples. All of the examples are actual examples. These examples are not to be construed as limiting the scope of the appended claims.

EXAMPLES

Example 1

Form N2 (Free Acid)

112.5 g of phosphoric acid, [3-[2-(4-benzoyl-1-piperazinyl)-1,2-dioxoethyl]-4,7-dimethoxy-1H-pyrrolo[2,3-c]pyridin-1-yl]methyl bis(1,1-dimethylethyl) ester was charged to a 2 L reactor equipped with an addition funnel and a mechanical stirrer. 1.1 L DCM was charged and agitation was set to 200 rpm. 200 ml TFA was charged over 5 minutes and the mixture was stirred for an additional 90 minutes until reaction was complete. The addition funnel was replaced with a distillation apparatus. The reaction volume was reduced to 500 ml via a reduced pressure distillation (550 torr, 30° C.). 400 ml MeOH was charged and the reaction volume was reduced to 500 ml via a reduced pressure distillation (500 torr, 30° C.). 400 ml THF was charged and the reaction mixture was stirred for no less than 12 hours. The slurry was filtered and rinsed with 500 mL THF. The sample was dried in a vacuum oven at 50° C. overnight. The weight of dry cake is 91.0 g. Yield was 97.9 M % Form N-2.

To form single crystal of Form N-2, the dry cake was recrystallized from MeOH/CH$_2$Cl$_2$.

Example 2

Form H-1 (Free Acid)

10 g of Form N-2 was added to a round-bottom flask equipped with a mechanical agitator. 650 mL of 60:40 solution of Ethanol/water was then charged. The mixture was then agitated at rpm 200. The temperature was increased to 70° C.-75° C. until all the Form N-2 was dissolved. The mixture was cooled to 5° C. over 4 hours. Agitation was continued for 6 hours. The sample was filtered and dried under vacuum at 50° C. Yield was 8.76 g Form H-1.

To form single crystal of Form H-1, Form N-2 was recrystalized from MeOH/H$_2$O.

Example 3

Form Hemi-Calcium Salt—H4-1

100 mg of Form N-2 was added to a scintillation vial with a magnetic stir-bar. 2 mL water was then added and stirring was initiated. 14.8 mg (0.5 eq) of Calcium acetate was added (as a 100 mg/mL solution in water). The resulting solution became almost clear yellow in few minutes. 1% seeds was charged and the mixture was stirred for 10 hours. The sample was filtered and dried under vacuum at 30° C., yielding Form Hemi-Calcium Salt—H4-1.

To form a single crystal of this form, Form Hemi-Calcium Salt—H4-1 obtained above was dissolved in NMP and distributed to 96 well plate so each well to have 1 mg of the salt and the solvent was evaporated under vacuum. In each well, desired solvent(s) were added in total volume of 200 uL (micro L). Among 96 conditions, 200 uL of water, 100 uL water/100 uL Heptane, 100 uL water/100 uL Isopropyl Acetate, 100 uL water/100 ul Cyclohexane, 100 uL water/100 uL MTBE, and 100 uL water/100 uL Toluene gave very nice colorless thick rods after 3 days at room temperature without agitation. The crystal from 100 uL water/100 uL Heptane well for Single crystal x-ray.

Example 4

Form Hemi-Magnesium Salt—H4-1

5 g of Form N-2 was added to a 3-neck round-bottom flask, equipped with a mechanical agitator. 100 mL water was added and agitation was started. 1.2 g (0.6 eq) of Mg acetate tetrahydrate was added as a 100 mg/mL solution in water. The resulting solution became clear yellow in about 5 minutes. 1% seeds was charged and the mixture was stirred for 10 hours. The sample was filtered and dried under vacuum at 30° C. Yield was 4.9 g Form Hemi-Magnesium Salt—H4-1.

To form a single crystal, the Form Hemi-Magnesium Salt—H4-1 material obtained above, was dissolved in Methanol and distributed to 96 well plate so each well to have 1 mg of the salt and the solvent was evaporated under vacuum. In each well, desired solvent(s) were added in total volume of 200 uL. The single crystal was formed after 10 days in 100 uL DMF/100 uL Heptane well left at room temperature without agitation.

Example 5

Form Mono-Magnesium Salt—P-3

3 g of Form N-2 was charged to a 3-neck round-bottom flask equipped with a mechanical agitator. 54 mL water was added and agitation was started (rpm=170). 1 eq of Mg ethoxide (645 mg) was added as a 50 mg/mL solution in water. The solution in the flask became clear yellow within a few minutes. The solution was stirred over 10 hours to form a slurry of P-3. The wet cake of P-3 was isolated by filtration on a Buchner funnel, and dried under conditions that would not result in loss of bound water (30° C. to 35° C., vacuum). Yield was 2.3 g.

Example 6

Form Hemi-Magnesium Salt—P-2

5 g of Form N-2 was added to a 3-neck round-bottom flask, equipped with a mechanical agitator. 100 mL water was added and agitation was initiated. 1.2 g (0.6 eq) of Mg acetate tetrahydrate was added as a 100 mg/mL solution in water. The solution in the flask became clear yellow in about 5 minutes. 1% seeds was charged and the mixture was stirred for 10 hours. The sample was filtered and dried under vacuum at 40° to 50° C.

Example 7

Form Mono-Lysine Salt—P-2

611 g of Form N-2 was chareged to a 10 L reactor equipped with a condenser and mechanical stirrer. 3875 ml of water was added followed by 168 g of lysine. The agitation rate was set to 100 rpm and the mixture was stirred for 1 hour. The mixture was heated to 50° C. and stirred for an additional hour until a hazy solution results (pH=4.55). The mixture was filtered through a 10 micron cuno filter into a 20 L reactor equipped with a condenser and mechanical stirrer. Agitation rate was set to 100 rpm and the mixture was heated to 50° C. 12 L of acetone was added keeping the reaction temperature above 45° C. then allow to heat to 50° C. 200 mg seeds was added. The mixture then slowly cooled to 20° C. over 5 hours, and then was stirred at 20° C. for no less then 12 hours. The slurry filtered and rinsed with 4 L of acetone, and dried in a vacuum oven at 25° C. under a slight stream of humid air overnight. The weight of the dry cake was 751. The yield was 96.4%.

Example 8

Form Mono-Lysine Salt—P-1

611 g of Form N-2 was chareged to a 10 L reactor equipped with a condenser and mechanical stirrer. 3875 ml of water was added followed by 168 g of lysine. The agitation rate was set to 100 rpm and the mixture was stirred for 1 hour. The mixture was heated to 50° C. and stirred for an additional hour until a hazy solution results (pH=4.55). The mixture was filtered through a 10 micron cuno filter into a 20 L reactor equipped with a condenser and mechanical stirrer. Agitation rate was set to 100 rpm and the mixture was heated to 50° C. 12 L of acetone was added keeping the reaction temperature above 45° C. then allow to heat to 50° C. 200 mg seeds was added. The mixture then slowly cooled to 20° C. over 5 hours, and then was stirred at 20° C. for no less then 12 hours. The slurry filtered and rinsed with 4 L of acetone, and dried in a vacuum with nitrogen vent at 50° C. overnight.

Example 9

Single Crystal X-Ray Measurements

Single Crystal X-ray Diffraction method was used to characterized samples obtained in Examples 1-4 using the procedure described below.

The results are shown in FIGS. 1, 6, 11, and 16.

Fractional atomic coordinates are shown in Tables 1-4.

Single Crystal Data (LVL)

Data were collected on a Bruker-Nonius (BRUKER AXS, Inc., 5465 East Cheryl Parkway Madison, Wis. 53711 USA) CAD4 serial diffractometer. Unit cell parameters were obtained through least-squares analysis of the experimental diffractometer settings of 25 high-angle reflections. Intensities were measured using Cu Kα radiation (λ=1.5418 Å) at a constant temperature with the θ-2 θ variable scan technique and were corrected only for Lorentz-polarization factors. Background counts were collected at the extremes of the scan for half of the time of the scan. Alternately, single crystal data were collected on a Bruker-Nonius Kappa CCD 2000 system using Cu Kα radiation (λ=1.5418 Å). Indexing and processing of the measured intensity data were carried out with the HKL2000 software package (Otwinowski, Z. & Minor, W. (1997) in *Macromolecular Crystallography*, eds. Carter, W. C. Jr & Sweet, R. M. (Academic, N.Y.), Vol. 276, pp. 307-326) in the Collect program suite (Collect Data collection and processing user interface: Collect: Data collection software, R. Hooft, Nonius B. V., 1998).

When indicated, crystals were cooled in the cold stream of an Oxford cryo system (Oxford Cryosystems Cryostream cooler: J. Cosier and A. M. Glazer, J. Appl. Cryst., 1986, 19, 105) during data collection.

The structures were solved by direct methods and refined on the basis of observed reflections using either the SDP (SDP, Structure Determination Package, Enraf-Nonius, Bohemia N.Y. 11716; Scattering factors, including f' and f", in the SDP software were taken from the "International Tables for Crystallography", Kynoch Press, Birmingham, England, 1974; Vol IV, Tables 2.2A and 2.3.1) software package with minor local modifications or the crystallographic package, MAXUS (maXus solution and refinement software suite: S. Mackay, C. J. Gilmore, C. Edwards, M. Tremayne, N. Stewart, K. Shankland. maXus: a computer program for the solution and refinement of crystal structures from diffraction data).

The derived atomic parameters (coordinates and temperature factors) were refined through full matrix least-squares. The function minimized in the refinements was $\Sigma_w(|F_o|-|F_c|)^2$. R is defined as $\Sigma||F_o|-|F_c||/\Sigma|F_o|$ while $R_w=[\Sigma_w(|F_o|-|F_c|)^2/\Sigma_w|F_o|^2]^{1/2}$ where w is an appropriate weighting function based on errors in the observed intensities. Difference maps were examined at all stages of refinement. Hydrogens were introduced in idealized positions with isotropic temperature factors, but no hydrogen parameters were varied.

Example 10

Powder X-ray Diffraction method was used to characterized samples obtained in Examples 1-8 using one of the procedures described below.

The results were shown in FIGS. 1, 6, 11, 16, 21, 24, 27, and 30.

PXRD (Philips)

About 200 mg were pack by the backloading method into a Philips powder X-ray diffraction (PXRD) sample holder. The sample was tranferred to a Philips MPD unit (45 KV, 40 mA, Cu Kα). Data were collected at room temperature in the 2 to 32 2-theta range (continuous scanning mode, scanning rate 0.03 degrees/sec., auto divergence and anti scatter slits, receiving slit: 0.2 mm, sample spinner: ON)

PXRD (GADDS-NB)

X-ray powder diffraction (PXRD) data were obtained using a Bruker C2 GADDS. The radiation was Cu Kα (40 KV, 50 mA). The sample-detector distance was 15 cm. Powder samples were placed in sealed glass capillaries of 1 mm or less in diameter; the capillary was rotated during data collection. Data were collected for $3 \leq 2\theta \leq 35°$ with a sample exposure time of at least 2000 seconds. The resulting two-dimensional diffraction arcs were integrated to create a traditional 1-dimensional PXRD pattern with a step size of 0.02 degrees 2θ in the range of 3 to 35 degrees 2θ.

PXRD (GADDS-LVL)

X-ray powder diffraction (PXRD) data were obtained using a Bruker GADDS (General Area Detector Diffraction System) manual chi platform goniometer. Powder samples were placed in thin walled glass capillaries of 1 mm or less in diameter; the capillary was rotated during data collection. The sample-detector distance was 17 cm. The radiation was Cu Kα (λ=1.5418 Ang). Data were collected for $3<2\theta<35°$ with a sample exposure time of at least 300 seconds.

Hybrid PXRD Patterns

"Hybrid" simulated powder X-ray patterns were generated as described in the literature (Yin. S.; Scaringe, R. P.; DiMarco, J.; Galella, M. and Gougoutas, J. Z., *American Pharmaceutical Review*, 2003, 6, 2, 80). The room temperature cell parameters were obtained by performing a cell refinement using the CellRefine.xls program. Input to the program includes the 2-theta position of ca. 10 reflections, obtained from the experimental room temperature powder pattern; the corresponding Miller indices, hkl, were assigned based on the single-crystal data collected at low temperature. A new (hybrid) PXRD was calculated (by either of the software programs, Alex or LatticeView) by inserting the molecular structure determined at low temperature into the room temperature cell obtained in the first step of the procedure. The molecules are inserted in a manner that retains the size and shape of the molecule and the position of the molecules with respect to the cell origin, but, allows intermolecular distances to expand with the cell.

Example 11

Differential Scanning Calorimetry (DSC)

DSC method was used to characterized samples obtained in Examples 1-8 using one of the procedure described below.

The results were shown in FIGS. 2, 7, 12, 17, 22, 25, 28, and 31.

DSC (Open Pan)

Differential scanning calorimetry (DSC) experiments were performed in a TA Instruments™ model Q1000 or 2920. The sample (about 2-6 mg) was weighed in an aluminum pan and recorded accurately recorded to a hundredth of a milligram, and transferred to the DSC. The instrument was purged with nitrogen gas at 50 mL/min. Data were collected between room temperature and 300° C. at 10° C./min heating rate. The plot was made with the endothermic peaks pointing down.

Example 12

Thermogravametric Analysis (TGA)

TGA method was used to characterized samples obtained in Examples 1-8 using one of the procedure described below.
The results were shown in FIGS. 3, 7, 13, 18, 23, 26, 29, and 32.

TGA (Open Pan)

Thermal gravimetric analysis (TGA) experiments were performed in a TA Instruments™ model Q500 or 2950. The sample (about 10-30 mg) was placed in a platinum pan previously tared. The weight of the sample was measured accurately and recorded to a thousand of a milligram by the instrument The furnace was purged with nitrogen gas at 100 mL/min. Data were collected between room temperature and 300° C. at 10° C./min heating rate.

Example 13

Moisture Sorption Isotherms

VIT method was used to characterized samples obtained in Examples 1-4 using one of the procedures described below.
The results were shown in FIGS. 4, 9, 14, 19, 24, 27, 30, and 33.

VTI

Moisture sorption isotherms were collected in a VTI (variable temperature isotherms) SGA-100 Symmetric Vapor Analyzer using about 10 mg sample. The sample was tested at 25° C. and 4, 5, 15, 25, 35, 45, 50, 65, 75, 85, and 95% RH. Equilibration at each RH was reached when the rate of 0.0003 wt %/min for 35 minutes was achieved.

VTI (EP)

Moisture sorption isotherms were collected in a VTI (variable temperature isotherms) SGA-100 Symmetric Vapor Analyzer using about 10 mg sample. The sample was tested at 25° C. and 10, 20, 30, 40, 50, 60, 70, 80, and 90% RH. Equilibration at each RH was reached when the rate of 0.0010 wt % in 5 min. or a total of 180 min. was achieved.

TABLE 1

Atomic coordinates (×10^4) and equivalent isotropic displacement parameters ($\text{Å}^2 \times 10^3$) for Form N-2.

| atom | x | y | z |
| --- | --- | --- | --- |
| P(1) | 8783(1) | 5970(1) | 4335(1) |
| O(1) | 7724(3) | 5199(3) | 4088(2) |
| O(2) | 8992(3) | 6122(4) | 5208(2) |
| O(3) | 8489(3) | 7269(4) | 4004(2) |
| O(4) | 9631(3) | 5321(4) | 4047(2) |
| O(5) | 7201(3) | 4718(3) | 5718(2) |
| O(6) | 3943(3) | 1483(3) | 4749(2) |
| O(7) | 3626(3) | 3203(4) | 2441(3) |
| O(8) | 4526(3) | 634(4) | 3154(2) |
| O(9) | −126(3) | −1591(4) | 3469(3) |
| N(1) | 5972(3) | 4731(4) | 4139(3) |
| N(2) | 6164(4) | 3074(4) | 5976(3) |
| N(3) | 2780(4) | 929(4) | 3099(3) |
| N(4) | 774(4) | 24(4) | 3171(4) |
| C(1) | 5288(4) | 4366(5) | 3498(3) |
| C(2) | 5857(4) | 3953(5) | 4743(3) |
| C(3) | 6400(5) | 3894(5) | 5498(3) |
| C(4) | 5347(5) | 2278(5) | 5732(4) |
| C(5) | 4788(4) | 2249(5) | 4997(3) |
| C(6) | 5065(4) | 3086(4) | 4466(3) |
| C(7) | 4718(4) | 3342(5) | 3669(3) |
| C(8) | 6729(4) | 5741(5) | 4165(3) |
| C(9) | 7827(5) | 4545(7) | 6456(3) |
| C(10) | 3607(5) | 702(5) | 5307(3) |
| C(11) | 3974(4) | 2722(5) | 3059(4) |
| C(12) | 3773(5) | 1321(5) | 3138(3) |
| C(13) | 2581(5) | −412(5) | 3161(4) |
| C(14) | 1525(6) | −768(6) | 2850(5) |
| C(15) | 914(6) | 1355(6) | 2978(5) |
| C(16) | 1933(5) | 1755(5) | 3288(5) |
| C(17) | −23(5) | −439(6) | 3462(4) |
| C(18) | −789(5) | 407(5) | 3722(4) |
| C(19) | −510(6) | 1278(6) | 4297(4) |
| C(20) | −1275(7) | 2026(7) | 4509(5) |
| C(21) | −2293(7) | 1929(7) | 4121(6) |
| C(22) | −2582(5) | 1043(8) | 3580(5) |
| C(23) | −1831(5) | 266(6) | 3388(3) |

TABLE 2

Atomic coordinates (×10^4) and equivalent isotropic displacement parameters ($\text{Å}^2 \times 10^3$) for Form H-1

| atom | x | y | z |
| --- | --- | --- | --- |
| P(1) | 1056(1) | 1301(1) | 4388(1) |
| O(1) | 1878(3) | 1915(1) | 5149(2) |
| O(2) | 2297(3) | 264(2) | 4469(2) |
| O(3) | 1341(3) | 1873(2) | 3330(2) |
| O(4) | −1045(3) | 1294(2) | 4708(2) |
| O(5) | 2603(3) | 3636(2) | 6366(2) |
| O(6) | 2635(3) | 6551(2) | 2987(2) |
| O(7) | 3423(4) | 5387(2) | 1390(2) |
| O(8) | 6925(4) | 3515(2) | 1440(2) |
| O(9) | −613(4) | 1662(2) | −639(2) |
| N(1) | 3861(3) | 3130(2) | 4387(2) |
| N(2) | 1983(3) | 5343(2) | 5620(2) |
| N(3) | 4217(4) | 3341(2) | 675(2) |
| N(4) | 2200(4) | 1998(2) | −128(2) |
| C(1) | 4300(4) | 3257(2) | 3390(2) |
| C(2) | 3169(4) | 4093(2) | 4623(2) |
| C(3) | 2564(4) | 4379(2) | 5557(2) |
| C(4) | 2002(4) | 6060(2) | 4771(2) |
| C(5) | 2580(4) | 5851(2) | 3836(2) |
| C(6) | 3186(4) | 4813(2) | 3747(2) |
| C(7) | 3917(4) | 4257(2) | 2946(2) |
| C(8) | 3826(5) | 2153(2) | 5032(2) |
| C(9) | 2082(5) | 3924(2) | 7331(2) |
| C(10) | 1832(5) | 7579(2) | 3052(3) |
| C(11) | 4043(5) | 4561(3) | 1866(3) |
| C(12) | 5152(6) | 3746(2) | 1300(3) |
| C(13) | 5292(5) | 2590(2) | 97(2) |
| C(14) | 4230(5) | 1681(3) | 194(3) |
| C(15) | 1144(5) | 2718(3) | 478(3) |
| C(16) | 2149(5) | 3636(3) | 432(3) |
| C(17) | 1175(6) | 1522(2) | −673(3) |
| C(18) | 2217(5) | 854(2) | −1370(2) |
| C(19) | 3890(5) | 1047(2) | −1929(2) |
| C(20) | 4645(6) | 439(3) | −2617(3) |
| C(21) | 3753(7) | −347(3) | −2777(3) |
| C(22) | 2087(6) | −553(3) | −2241(3) |
| C(23) | 1315(5) | 44(3) | −1539(3) |
| O(1W) | 568(3) | 6387(2) | 7149(2) |

TABLE 3

Atomic coordinates (×10^4) and equivalent isotropic displacement parameters (A^2 × 10^3) for Form Hemi-Calcium Salt H4-1

| atom | x | y | z |
|---|---|---|---|
| Ca(1) | 0 | 0 | 5000 |
| P(1) | 3912(1) | −478(1) | 3522(1) |
| O(1) | 3366(2) | −878(1) | 2738(1) |
| O(2) | 2443(2) | −820(1) | 4318(1) |
| O(3) | 6008(2) | −831(1) | 3661(1) |
| O(4) | 3602(2) | 748(1) | 3100(1) |
| O(5) | 2712(2) | −1580(1) | 1002(1) |
| O(6) | 2093(3) | 2431(1) | −1480(1) |
| O(7) | 1433(3) | 3692(1) | −334(1) |
| O(8) | −2002(3) | 3332(2) | 1217(2) |
| O(9) | 5415(2) | 4567(2) | 3029(1) |
| N(1) | 1406(3) | 221(1) | 1552(1) |
| N(2) | 3020(3) | −426(1) | −501(1) |
| N(3) | 814(3) | 3686(2) | 1638(2) |
| N(4) | 2649(3) | 5007(2) | 2264(1) |
| C(1) | 907(3) | 1221(2) | 1489(2) |
| C(2) | 1966(3) | 228(2) | 673(1) |
| C(3) | 2581(3) | −607(2) | 373(1) |
| C(4) | 2859(3) | 573(2) | −1112(2) |
| C(5) | 2274(3) | 1432(2) | −879(1) |
| C(6) | 1817(3) | 1255(2) | 65(1) |
| C(7) | 1152(3) | 1898(2) | 602(1) |
| C(8) | 1457(3) | −657(2) | 2406(2) |
| C(9) | 3350(4) | −2419(2) | 681(2) |
| C(10) | 3040(4) | 2643(2) | −2366(2) |
| C(11) | 904(4) | 3023(2) | 379(2) |
| C(12) | −205(4) | 3366(2) | 1128(2) |
| C(13) | −164(4) | 4022(2) | 2368(2) |
| C(14) | 508(4) | 5057(2) | 2300(2) |
| C(15) | 3574(4) | 4700(2) | 1508(2) |
| C(16) | 2964(4) | 3661(2) | 1587(2) |
| C(17) | 3692(4) | 4933(2) | 2973(2) |
| C(18) | 2766(4) | 5370(2) | 3669(2) |
| C(19) | 1871(5) | 6371(2) | 3421(2) |
| C(20) | 1213(6) | 6789(3) | 4085(2) |
| C(21) | 1426(5) | 6213(3) | 4989(2) |
| C(22) | 2297(4) | 5224(3) | 5241(2) |
| C(23) | 2980(4) | 4798(3) | 4584(2) |
| O(1W) | 2017(3) | 1414(2) | 4731(2) |
| O(2W) | 1626(3) | −746(2) | 6392(1) |
| O(3W) | 4000(3) | −2321(2) | 6035(2) |
| O(4W) | 5837(3) | 1571(2) | 1647(1) |

TABLE 4

Atomic coordinates (×10^4) and equivalent isotropic displacement parameters (A^2 × 10^3) for Form Hemi-Magnesium Salt H4-1

| Atom | x | y | z |
|---|---|---|---|
| Mg(1) | 0 | 0 | 5000 |
| P(1) | 3819(4) | −403(2) | 3586(2) |
| O(1) | 3374(9) | −808(4) | 2778(4) |
| O(2) | 2197(9) | −678(5) | 4326(4) |
| O(3) | 5896(9) | −801(5) | 3804(5) |
| O(4) | 3605(9) | 811(5) | 3136(4) |
| O(5) | 2707(9) | −1548(4) | 991(4) |
| O(6) | 2148(10) | 2399(5) | −1495(4) |
| O(7) | 1623(12) | 3662(5) | −335(5) |
| O(8) | −1939(10) | 3354(5) | 1196(5) |
| O(9) | 5439(11) | 4626(7) | 3010(6) |
| N(1) | 1449(10) | 252(5) | 1547(5) |
| N(2) | 2998(10) | −423(5) | −523(5) |
| N(3) | 895(12) | 3717(6) | 1628(6) |
| N(4) | 2661(12) | 5074(6) | 2222(5) |
| C(1) | 1003(13) | 1255(7) | 1486(6) |
| C(2) | 2006(12) | 248(6) | 669(5) |
| C(3) | 2582(12) | −589(6) | 353(6) |
| C(4) | 2842(13) | 557(7) | −1126(6) |
| C(5) | 2321(12) | 1409(7) | −887(5) |
| C(6) | 1872(12) | 1263(6) | 57(6) |

TABLE 4-continued

Atomic coordinates (×10^4) and equivalent isotropic displacement parameters (A^2 × 10^3) for Form Hemi-Magnesium Salt H4-1

| Atom | x | y | z |
|---|---|---|---|
| C(7) | 1238(13) | 1910(6) | 590(6) |
| C(8) | 1454(13) | −616(7) | 2430(6) |
| C(9) | 3301(14) | −2392(7) | 665(6) |
| C(10) | 3088(16) | 2589(8) | −2379(7) |
| C(11) | 1044(14) | 3013(8) | 374(6) |
| C(12) | −106(15) | 3379(7) | 1113(7) |
| C(13) | −119(15) | 4063(9) | 2356(7) |
| C(14) | 505(15) | 5105(8) | 2271(7) |
| C(15) | 3654(15) | 4757(8) | 1483(7) |
| C(16) | 3065(14) | 3714(8) | 1564(8) |
| C(17) | 3718(18) | 5000(8) | 2944(7) |
| C(18) | 2734(15) | 5460(9) | 3637(7) |
| C(19) | 1831(18) | 6443(8) | 3397(8) |
| C(20) | 1130(20) | 6866(9) | 4070(9) |
| C(21) | 1350(20) | 6294(13) | 4976(9) |
| C(22) | 2230(17) | 5312(13) | 5225(8) |
| C(23) | 2944(16) | 4885(10) | 4575(8) |
| O(1W) | 1646(11) | 1310(5) | 4674(5) |
| O(2W) | 1523(11) | −681(5) | 6216(4) |
| O(3W) | 4004(14) | −2341(7) | 6043(7) |
| O(4W) | 6012(11) | 1556(5) | 1708(5) |

What is claimed is:

1. The N-2 crystalline form of compound (I),

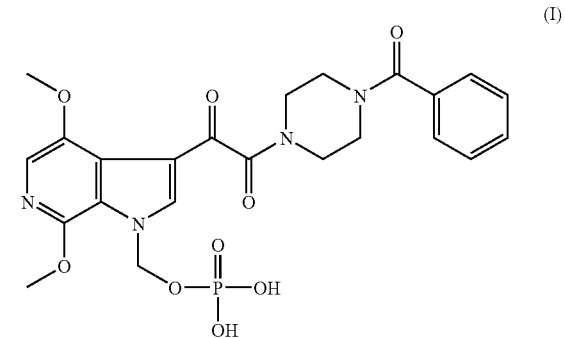

(I)

said form being in a single crystal form, and wherein said form is substantially pure.

2. The crystalline form according to claim 1 characterized by unit cell parameters substantially equal to the following:

| | |
|---|---|
| Cell dimensions: | a = 12.922 Å |
| | b = 10.744 Å |
| | c = 17.803 Å |
| | α = 90 degree |
| | β = 101.002 degree |
| | γ = 90 degree |
| Space group | P2$_1$/C, monoclinic |
| Molecules/unit cell | 4 | wherein said crystalline form is at a temperature of about 20° C. to about 25° C.

3. The crystalline form according to claim 1 characterized by a powder x-ray diffraction pattern comprising four or more 2θ values (CuKα λ=1.5418 Å) selected from the group consisting of 9.7±0.2, 10.1±0.2, 10.8±0.2, 12.5±0.2, 13.9±0.2, 15.6±0.2, 17.3±0.2. and 21.7±0.2, at a temperature of about 20° C. to about 25° C.

4. The crystalline form according to claim 3 further characterized by a powder x-ray diffraction pattern comprising five or more 2θ values (CuKα λ=1.5418 Å) selected from the group consisting of 9.7±0.2, 10.1±0.2, 10.8±0.2, 12.5±0.2, 13.9±0.2, 15.6±0.2, 17.3±0.2. and 21.7±0.2, at a temperature of about 20° C. to about 25° C.

5. The crystalline form according to claim 1 characterized by an X-ray powder diffraction (PXRD) pattern, at a temperature of about 20° C. to about 25° C., substantially in accordance with that shown in FIG. 1.

6. The crystalline form according to claim 1 characterized by a differential scanning calorimetry (DSC) thermogram substantially in accordance with that shown in FIG. 2.

7. The crystalline form according to claim 1 characterized by a thermo gravimetric analysis (TGA) diagram substantially in accordance with that shown in FIG. 3.

Figure 5:
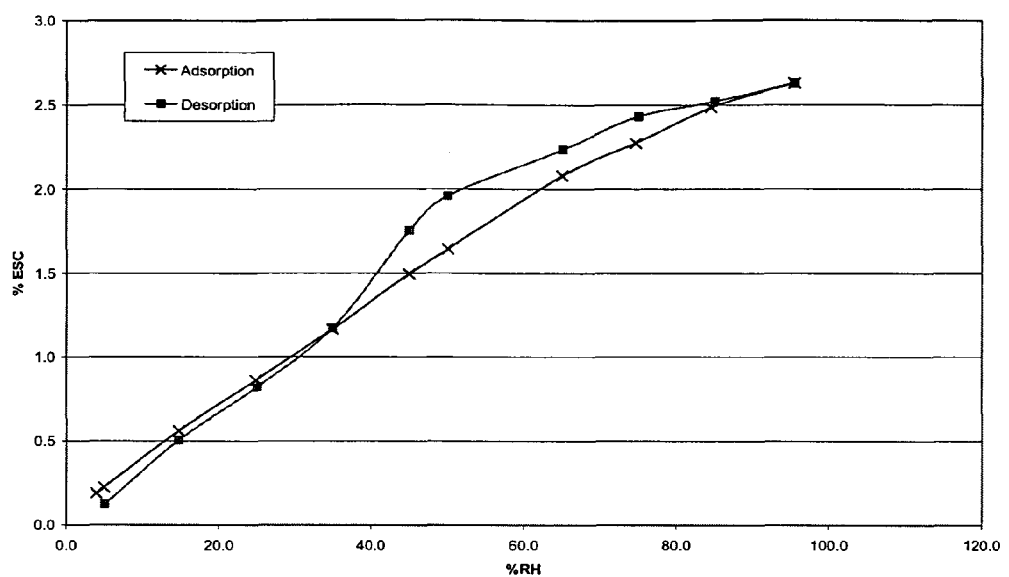
FIG. 5. illustrates moisture-sorption isotherms of Form N-2 of Compound (I).
Figure 6:
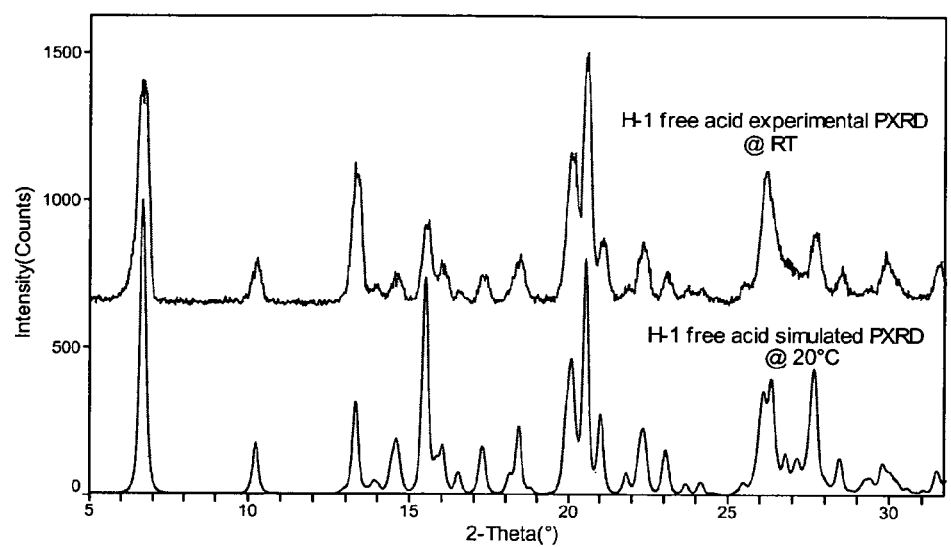
FIG. 6. illustrates experimental and simulated powdered X-ray diffraction patterns of Form H-1 of Compound (I).
Figure 7:
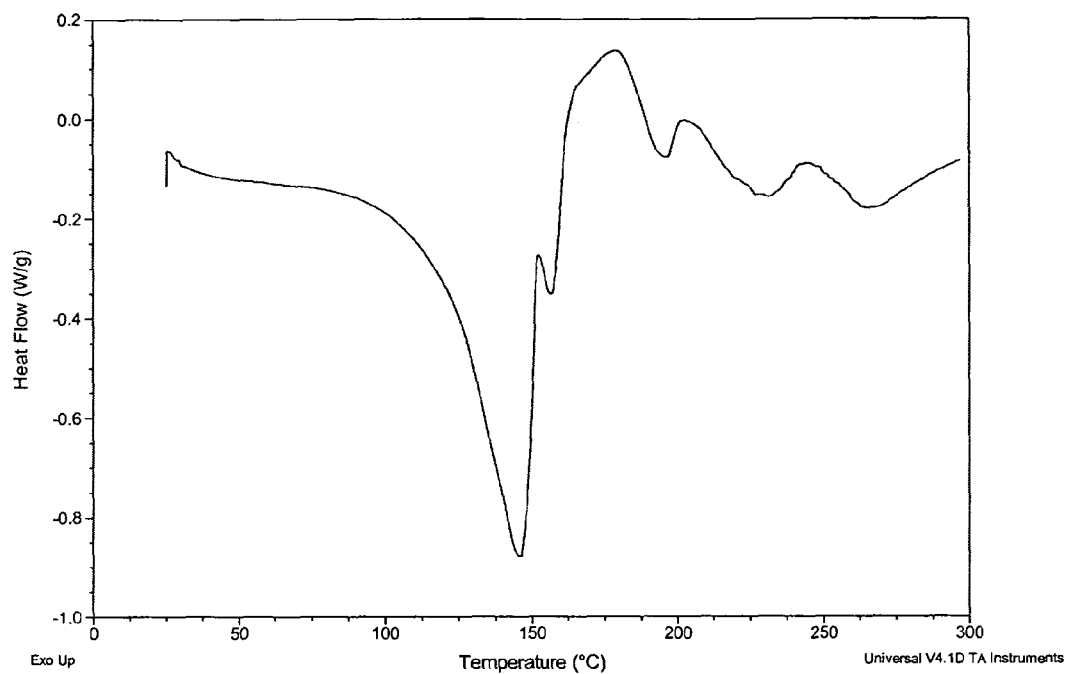
FIG. 7. illustrates differential scanning calorimetry pattern of Form H-1 of Compound (I).
Figure 8:
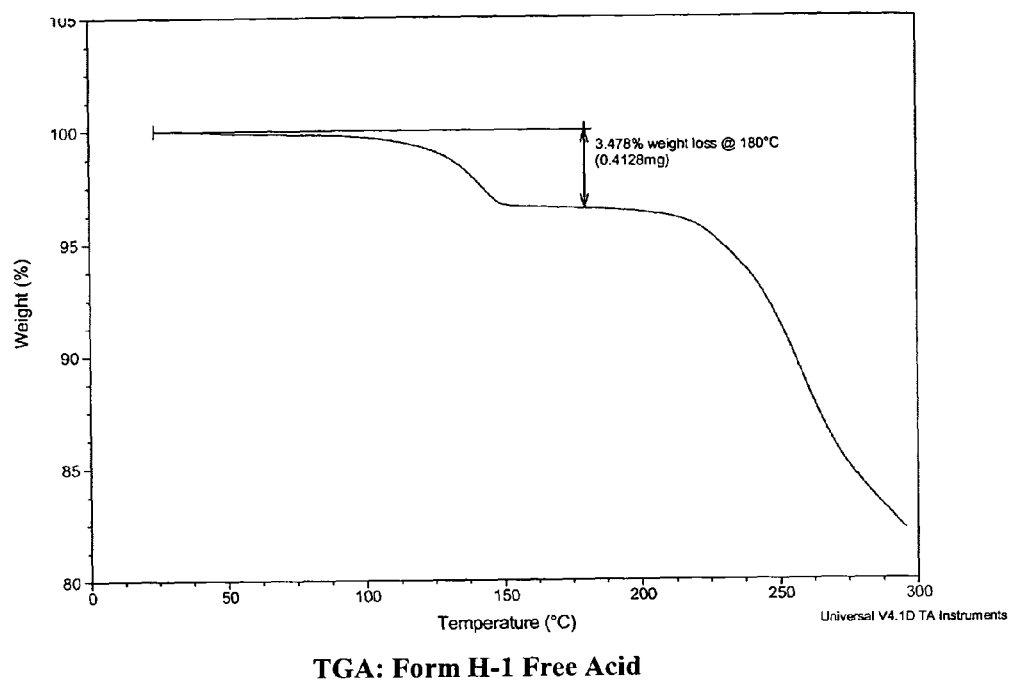
FIG. 8. illustrates thermogravimetric analysis pattern of Form H-1 of Compound (I).

8. The crystalline form according to claim 1 characterized by moisture-sorption isotherms substantially in accordance with that shown in FIG. 5.

9. A pharmaceutical composition comprising the crystalline form according to claim 1 and a pharmaceutically acceptable carrier or diluent.

10. A method of treating AIDS or HIV infection in a mammal comprising administering to the mammal a therapeutically-effective amount of the crystalline form according to claim 1.

11. The method according to claim 10, wherein the mammal is a human.

12. A composition comprising at least 5 weight % of the crystalline form according to claim 1, based the weight of the composition.

* * * * *